United States Patent
Quady

(10) Patent No.: US 8,675,835 B2
(45) Date of Patent: *Mar. 18, 2014

(54) INTERACTIVE PROPERTY COMMUNICATION SYSTEM

(71) Applicant: Curtis E. Quady, Englewood, FL (US)

(72) Inventor: Curtis E. Quady, Englewood, FL (US)

(73) Assignee: Curtis E. Quady, Englewood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/659,772

(22) Filed: Oct. 24, 2012

(65) Prior Publication Data

US 2013/0287185 A1     Oct. 31, 2013

Related U.S. Application Data

(63) Continuation of application No. PCT/US2012/039962, filed on May 30, 2012, which is a continuation-in-part of application No. 13/458,757, filed on Apr. 27, 2012.

(60) Provisional application No. 61/491,288, filed on May 30, 2011.

(51) Int. Cl.
H04M 11/00     (2006.01)

(52) U.S. Cl.
USPC ............ 379/90.01; 379/38; 379/49; 455/457; 455/575.7

(58) Field of Classification Search
USPC ......................... 379/90; 455/414, 557, 575.7
See application file for complete search history.

(56) References Cited

U.S. PATENT DOCUMENTS

| | | | |
|---|---|---|---|
| 6,894,609 B2 | 5/2005 | Menard et al. |
| 6,967,562 B2 | 11/2005 | Menard et al. |
| 8,149,095 B2 | 4/2012 | Hayashi et al. |
| 8,548,439 B2 | 10/2013 | Quady |
| 2003/0091158 A1 | 5/2003 | Puchek et al. |
| 2006/0002355 A1 | 1/2006 | Baek et al. |
| 2006/0154642 A1 | 7/2006 | Scannell, Jr. |
| 2006/0277075 A1 | 12/2006 | Salwan |
| 2008/0146158 A1 | 6/2008 | Pan et al. |
| 2008/0153483 A1 | 6/2008 | Abu-Amara |
| 2010/0015926 A1 | 1/2010 | Luff |
| 2011/0028121 A1 | 2/2011 | Sennett |
| 2012/0309364 A1 | 12/2012 | Quady |

FOREIGN PATENT DOCUMENTS

WO     WO-2012166780 A1     12/2012

OTHER PUBLICATIONS

"U.S. Appl. No. 13/458,757 , Response filed Jan. 23, 2013 to Non Final Office Action mailed Oct. 26, 2012", 11 pgs.
"U.S. Appl. No. 13/458,757, Non Final Office Action mailed Oct. 26, 2012", 11 pgs.
"International Application Serial No. PCT/US2012/039962, International Search Report mailed Sep. 19, 2012", 4 pgs.
"International Application Serial No. PCT/US2012/039962, Written Opinion mailed Sep. 19, 2012", 4 pgs.

(Continued)

*Primary Examiner* — Joseph J Nguyen
(74) *Attorney, Agent, or Firm* — Schwegman, Lundberg & Woessner, P.A.

(57) ABSTRACT

Disclosed herein, among other things, are apparatus and methods for interactive property communication. In various embodiments, an interactive property communication system includes two or more property communication nodes (PCNs) each adapted for coupling to an electrical service. PCNs include a radio transceiver for communications with a broker service adapted for controlling communications with one or more PCNs.

26 Claims, 12 Drawing Sheets

(56) References Cited

OTHER PUBLICATIONS

"U.S. Appl. No. 13/458,757, Notice of Allowance mailed Jun. 25, 2013", 17 pgs.
"U.S. Appl. No. 13/659,720, Non Final Office Action mailed Oct. 10, 2013", 23 pgs.
"U.S. Appl. No. 13/659,798, Examiner Interview Summary mailed Aug. 12, 2013", 2 pgs.
"U.S. Appl. No. 13/659,798, Non Final Office Action mailed Aug. 19, 2013", 16 pgs.
"U.S. Appl. No. 13/659,807, Non Final Office Action mailed Sep. 16, 2013", 6 pgs.
"International Application Serial No. PCT/US2012/039962, International Preliminary Report on Patentability mailed Dec. 12, 2013", 6 pgs.

INTERACTIVE PROPERTY COMMUNICATION SYSTEM

This application is a continuation under 35 U.S.C. §111(a) of and claims the benefit of priority to International Patent Application Serial No. PCT/US2012/039962, filed on May 30, 2012, which is a continuation-in-part of U.S. patent application Ser. No. 13/458,757, entitled "INTERACTIVE PROPERTY COMMUNICATION SYSTEM," and filed on Apr. 27, 2012, which in turn claims the priority benefit of U.S. Provisional Patent Application No. 61/491,288, filed May 30, 2011, the entire contents of each being incorporated herein by reference.

RELATED APPLICATIONS

This application is related to U.S. Pat. No. 6,894,609, issued on May 17, 2005 and U.S. Pat. No. 6,967,562, issued on Nov. 22, 2005, both of which are incorporated herein by reference in their entirety.

TECHNICAL FIELD

This document relates generally to information communication systems and more particularly to interactive communication systems for user property.

BACKGROUND

It is thought that the average person in the United States (2010 population greater than 308 million according to the United States Census Bureau) normally spends almost one-half of their time in their "household" (greater than 113,000,000 in 2010—United States Census Bureau) owned, rented or living with others (a convenient term used to represent where a person calls their "home"). The elderly and disabled spend more to all of their time in their home. If the weather is inclement, a person is sick, without a job, has little income, or with other similar or adverse happenings or conditions, the time spent in their home would be substantially more.

When a person does leave their home it is common for them to carry a portable cell phone ("PCP"), portable smart phone ("PSP") or some other such similar portable communication device—commonly cell phones ("CP") (of 308,000,000 citizens, 234,000,000 owned CP's—"comScore") that allows for a user ("user") to, among other functions, make and receive voice calls, e-mails, text or other short messages, videos, pictures, music, voice, data, graphics, and in general, send and receive other information, along with carrying in the CP personal alarm clocks, calendars, reminders, contact name, business, etc. lists, having and using an internet web browser and entering a web address, selecting speed connections through a personalized app, using voice commands, etc. to connect to a destination web site, etc. to search, view, etc. and obtain requested or other useful, in general, information in various forms.

In most circumstances when the user leaves their home they have their CP powered up or turned on in some mode that they can be aware of some to all inbound e-mails, telephone calls, messages, data, etc., broadly called inbound information. But many times the user must turn the CP off, or at least turn the CP to some form of diminished alert status to incoming information—thus rendering the CP in many cases partially to completely inoperative to inbound information. Examples of when the user must turn off or to a diminished alerting status would be in a meeting, in church, in a movie theater, to name but a few likely situations. Or the user may simply elect to not have the CP on, not be in useable proximity, may even have left it somewhere or have had the battery drained below operating levels, thus rendering the CP temporarily or permanently unusable for any communications—in or out.

When a person returns home they generally set their CP somewhere in a single location, thus making the CP usage or range of operability extremely small, or perhaps not operational at all. In some cases in the US and in the World, some people return home and do not have either a CP or home land-line telephone provider service. This circumstance may be one of choice, or because one or both of the services to the CP and/or land-line telephone may be inoperative because of numerous reasons. In either of these cases, the user(s) would be totally without telephone-type communication—in or out bound.

In the past it was common for the US household and its inhabitants (each household has 2.6 inhabitants—US Census Bureau 2010 totaling more than 294,000,000 population in households) to have a telephone land-line. In 1999 there were 186,000,000 home lines. But since 2000 the number of land-lines has fallen in number 4 to 6% every year since. And even more, today 25% of homes have abandoned their landlines (National Health Interview Survey). 22.9% of adults live in homes that have CP but no land-line telephone. The number of wireless (CP) only homes grew 4.3% between 2008 and 2009. Younger users are more likely to live in CP only homes: 48.6% of people aged 25 - 29, 33% of people aged 18-24 and 30-34. More interesting are those adults living in poverty live in 36.3 CP only homes, and amazingly 1.7% of US adults have no phone—CP or land-line. A review of the telephone company's revenue from home land-lines shows a similar story; continue decreasing numbers of home land-lines and revenue, along with increasing revenue from CP service. In the past, households treated the telephone company as a utility—a must, but today what with higher energy, food, etc. costs, loss or reduction in work and earnings or stagnant income, etc., consumers are saying land-lines are an expendable luxury that can only call from home not anywhere the user is. Even abandoned and foreclosed homes are contributing to abandoned or cancelled land-line service, not to be often placed back into service with a new owner. Even new homes now come with 'optional' telephone wiring.

People at home are very often not in close contact with either type of telephone—CP or landline because they are in a different or distant room, indisposed, disabled, aged or slow of movement, sleeping or are outside in their yard where they cannot hear either phone 'ring.' Additionally people may not be able to hear the phone 'ring' because the volume is turned down or off by conscious switching or by a depleted battery, the phone and/or network is inoperable, or the CP is on vibrate. Or people at home can perhaps hear either phone 'ring' but cannot answer because they are indisposed, have their arms full or cannot answer for numerous other reasons.

One attempt to provide communications with persons at home was taken with prior art home security systems that provide an emergency communication controlled by an alarm panel at the home of the individual. However, such communications are restricted to situations where the person is at the location of the alarm panel in the home.

Consequently, cell phones are intended to provide communications to a person, but those communications have the foregoing issues. Accordingly, there is a need in the art for providing an improved interactive communication system for dwellings and other places occupied by people.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present invention provides a system for bidirectional communication that can programmably control communications to and from places where people, live, work, monitor, recreate, safeguard or protect, or just generally occupy. For the purposes of this application, each such place shall be called a "property." The use of the term property shall not be limited to a structure, but can include areas outside of a structure, such as a back yard or playground. Thus, the property can be indoors or outdoors, or combinations thereof. Any variety of dwelling places, workplaces, storage places, and play areas are included as some examples of the scope of the concept of property for purposes of this application. The system includes a content control service that acts as a broker for the type of communications sent to the property and the information coming from the property to at least one agency (a "broker service"). In various applications, the broker service is programmable for indicating a plurality of parameters for communications, including preferences of communications.

The present system allows for a communications to a home, office, warehouse, factory, or any number of properties. It allows the resident or subscriber the ability to control communications as they move from one location at the property to another, as long as each such location in the property has at least one Property Communications Node (PCN) that allows for two-way communications between the person at the property and the broker service. Depending on the application a plurality of PCNs may be employed. It is understood that in some applications a single PCN may suffice.

Communications System

Figure 1:
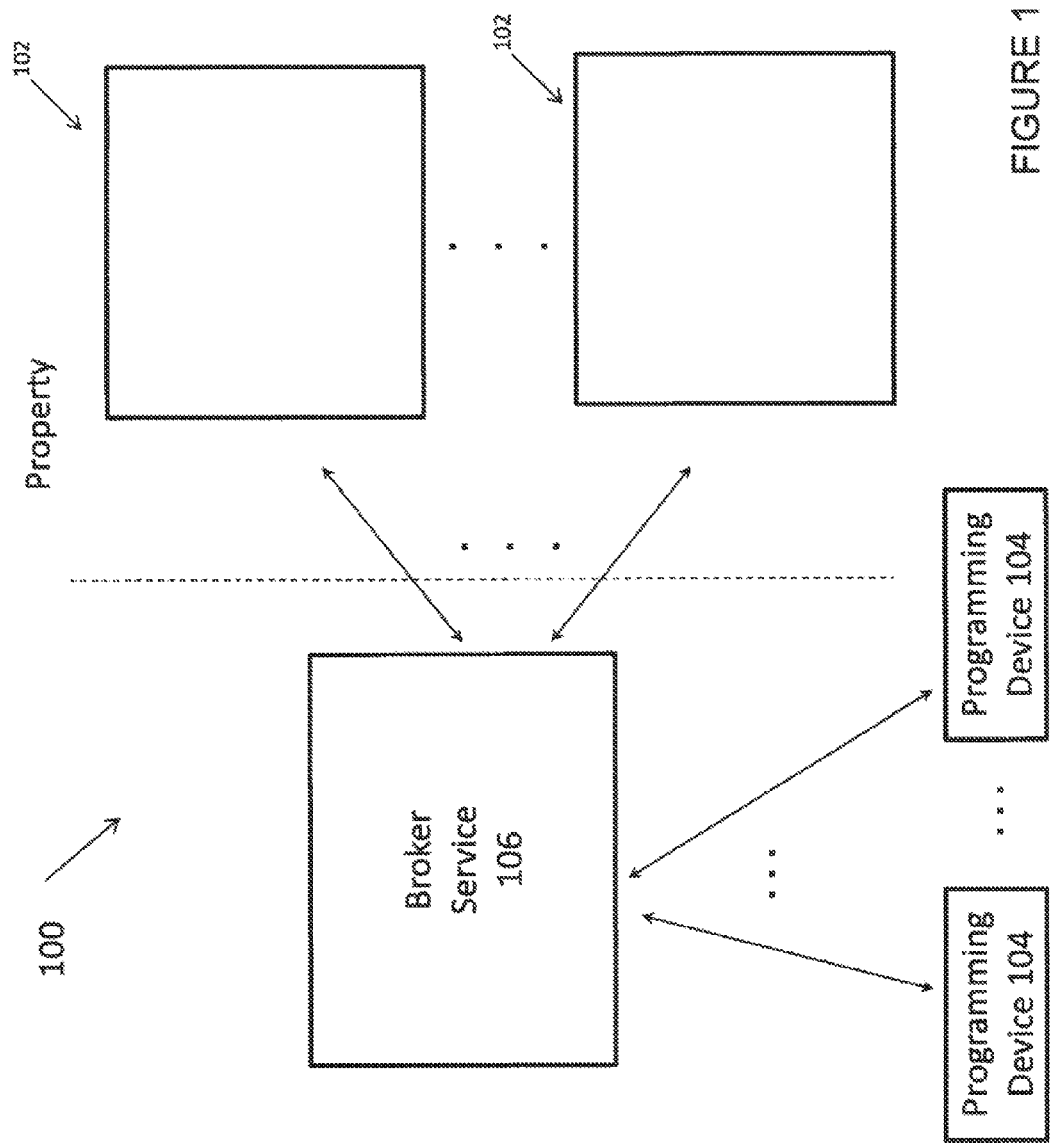
FIGS. 1-5, and 12 show some different embodiments of an interactive property communication system according to various embodiments of the present subject matter.

FIG. 1 shows a block diagram of an overview of one embodiment of a system of the present subject matter. The system 100 includes a broker service 106 that can be configured by one or more programming devices 104 and which is in communication with one or more property communication nodes (PCNs) 102. In various embodiments, the PCNs 102 are devices that communicate with sensors at the property and provide annunciation functions for the subscriber(s) at the property. Further aspects of the communications system are set forth in this document and the examples given herein are intended to demonstrate the present subject matter and not in an exhaustive or limited sense.

Broker Service

The broker service may have a variety of communications options and may be deployed across a number of and variety of different apparatus. It is understood that the broker service 106 can communicate with one or a plurality of PCNs. It is understood also that the broker service 106 can communicate to a property or a plurality of different properties. Such communications can be to a single subscriber or to a plurality of subscribers. For example, the broker service can communicate with a single PCN at the property of a single subscriber. It can communicate to several property owned or controlled or rented or merely occupied by the same subscriber. These same communications can take place with any number of PCNs at each property, as long as there is at least one PCN at each property.

For example, the broker service can communicate with a single PCN at the property of a plurality of subscribers. It can communicate to several property owned or controlled or rented or merely occupied by a plurality of subscribers. These same communications can take place with any number of PCNs at each property, as long as there is at least one PCN at each property.

In various embodiments, the broker service is connected to the PCNs at the property. Such connection can be wired, wireless, or combinations thereof. One preferred embodiment is a wireless connection to the PCNs 102 and a wireless or wired connection to the programming devices 104. The connection can be a network connection adapted for a variety of uses and users or it can be a dedicated connection. Any variety of wireless protocols can be employed including, but not limited to, cellular, sms messaging, WiFi, Bluetooth™, and proprietary wireless protocols. Wired connections include various types of typical Internet connections, local area network connections, intranet connections, public switched telephone network (PTSN) connections, and proprietary network connections.

In one preferred embodiment, the broker service 106 is connected to the Internet. It is also connected to the telephone network, including wireless cellular networks. It has a software interface that affords subscribers secure access via a dedicated programming interface or via a general communication interface with controlled access. In various embodiments, the broker service 106 includes a database for each subscriber. The database includes some private information about the subscriber and application-specific information. For example, assuming the particular application relates to medical monitoring, the entry for the subscriber can include medical information about the subscriber, and information about the timing and nature of the medical monitoring that must be done for that subscriber. To demonstrate one example, the subscriber database can include the following (however, the subscriber database can include different and other information and is not limited to this example):

a. Subscriber Name: John Smith
b. Subscriber Medical Monitoring Notification: "Did you take your insulin?"
c. Frequency of Notification: 3 times a day
d. Notification times: 9:00 a.m., 1:00 p.m., 6:00 p.m.

e. Notification method: Transmit verbal message to PCN
f. Confirmation Codes: Code 1 "Press 1 or say one for Yes," Code 2 "Press 2 or say two for No," Code 3 "Press 3 or say Need Help" for Need Help
g. Confirmation Method: Voice Prompt and Voice Recognition at Property
h. Contingency actions by broker service based on results from f.:
  i. If Need Help, then
    1. Contact 911 Emergency Systems with Subscriber Name and Subscriber PCN Address and Subscriber Medical Information
    2. Contact Daughter, Mary Smith
      a. Call (613) 333-3099
      b. Email: msmith338@aol.com
  ii. If No, then the broker service will contact subscriber's Daughter, Mary Smith at (613) 333-3099
  iii. Authorized Access Contact: Daughter, Mary Smith at (613) 333-3099 (this allows the trusted daughter the ability to access all of the subscriber's information).

Therefore, the broker service 106 provides a confidential, trusted resource for monitoring and controlling communications for each subscriber. It provides a barrier to unwanted communications from services and individuals who would like to use the communications to their advantage and allows the subscriber to control such features. It provides the broker service 106 an ability to block unwanted communications (as defined by the subscribership) and to allow preferred communications to and from the subscriber with third parties (other individuals, services, entities) via the PCN or PCNs 102.

Figure 8:
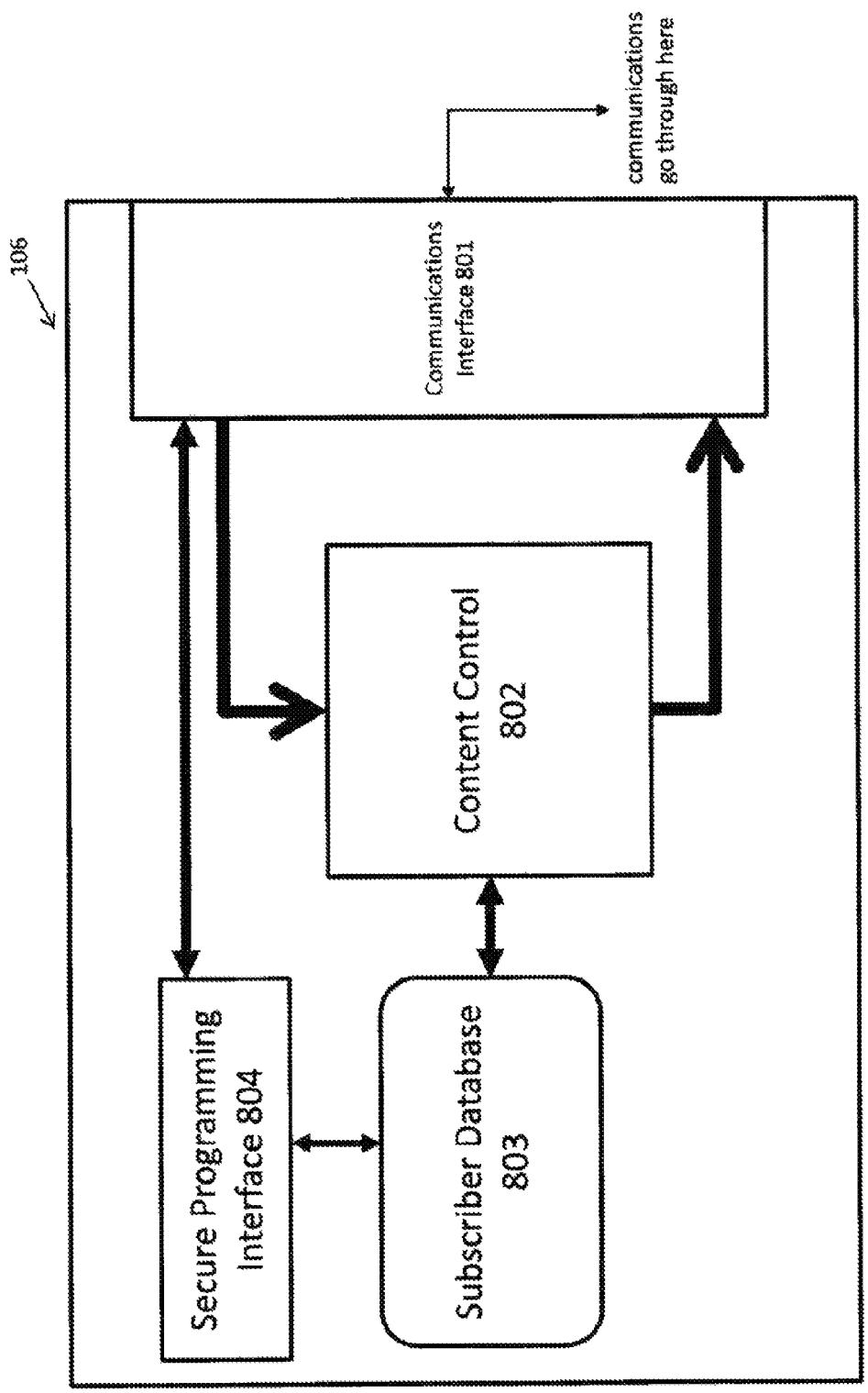
FIGS. 8 and 9 show some variations of different embodiments of broker service block diagrams according to various embodiments of the present subject matter.
Figure 9:
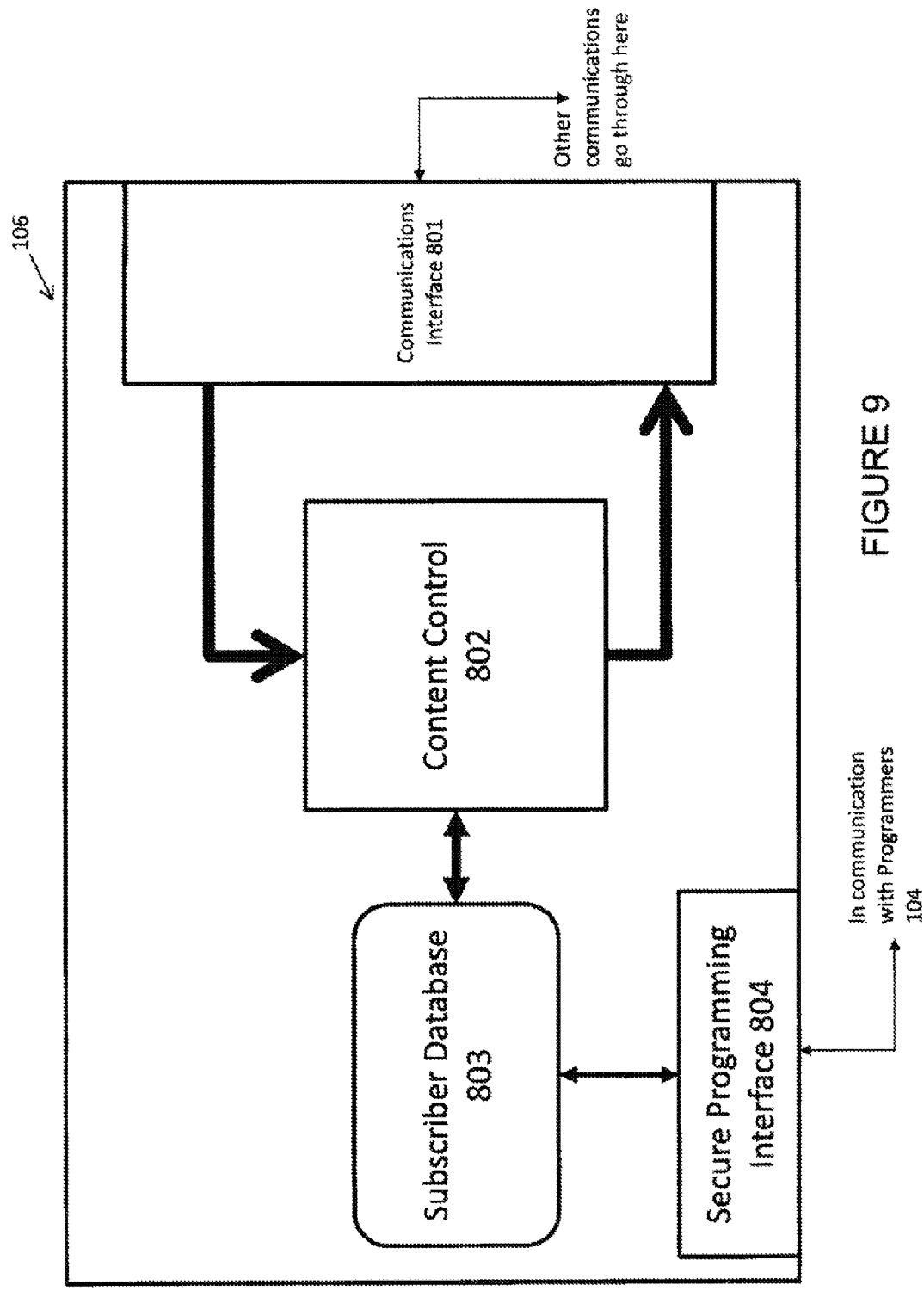

In various embodiments, the broker service 106 has a database for subscriber information 803, and a content controller 802 for filtering content through the broker service 106, as shown in FIGS. 8 and 9. The embodiment of FIG. 8 includes a common communication interface 801 which controls communications to and from subscribers, programming devices, service providers and content sources. The broker service 106 provides controlled access by the subscribers using secure programming interface 804. Programming devices 104 can be used to communicate to the interface 801 and provide the necessary authentication codes or information to access the subscriber database 803 via secure programming interface 804. This allows configurable and programmable ways for different trusted entities to program the subscriber database 803 or portions of it. For example, subscribers via programming devices 104 can program the subscriber database 803 (and access information therefrom) using a security code, password, or other controlled access. Other subscriber information can be accessed and programmed from a portion of the subscriber database by trusted services, for example in the application involving home security a trusted monitoring service can access subscriber information to update its alert database, or to query the subscriber for customized access information. For example, the trusted service provider (e.g., monitoring service) can provide queries to the subscriber who is their customer to request updates for monitoring and alerts. The subscriber can receive such queries at their respective PCN(s) 102 and respond. The information can be stored in the subscriber database under an entry for that monitoring service. For example, if a fire is detected, besides contacting emergency support services, the system is programmed to contact the subscriber at her cell phone number (613) 337-2013 and send a text message to a predetermined internet address with the fire detection information. Of course, the broker service could contact any neighbor, friend, or other PCN of such persons.

The broker service can use any PCN on the network to distribute information. In some applications, only the broker service knows where the subscriber is at and the broker service can take appropriate actions based on the predetermined programming by the subscriber. The broker system can provide these contingency options for the subscriber no matter where the subscriber is at. One such application can be in travel. For example a hotel fitted with PCNs could be used by any subscriber to "follow" his or her person along their travels and any emergency or other communications can relatively seamlessly be conducted while the subscriber is at the hotel or other establishment fitted with a PCN. The broker service can know where the person is at physically and address any situation as programmed by the subscriber in any event.

The embodiment of FIG. 9 includes at least two communication interfaces. A first communications interface 801 is used generally for incoming information from a variety of sources and for outgoing information to a variety of destinations, based on content controller 802. In this embodiment, the secure programming interface 804 is directly accessible for subscribers and other users of programming devices 104. The secure programming interface 804 allows access to the subscriber database 803.

Figure 10:
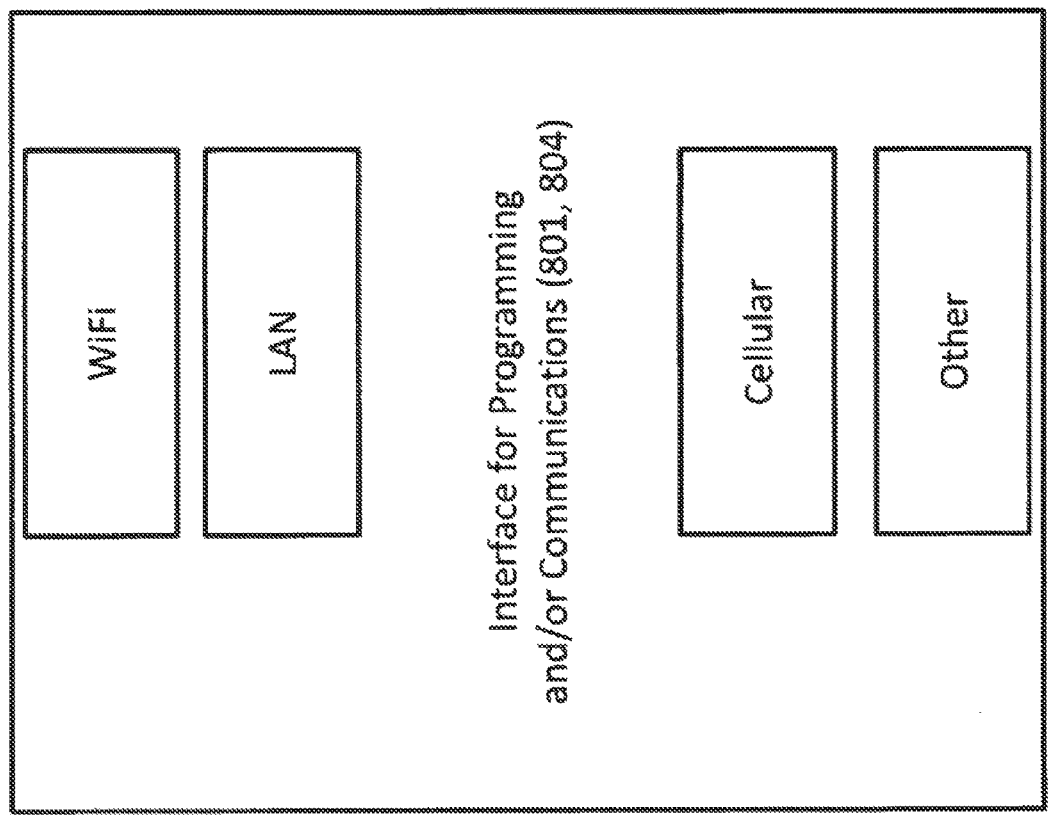
FIG. 10 shows one example of different interfaces of a broker service according to various embodiments of the present subject matter.

FIG. 10 demonstrates that for either interface 801 or 804, any variety of wired and wireless protocols can be employed including, but not limited to, cellular, LAN, WiFi, and other protocols. FIG. 10 demonstrates just some of the protocols available. It is understood that a variety of other protocols can be employed, including, but not limited to, SMS messaging, Bluetooth™, and other proprietary wireless protocols. Other wired connections include, but are not limited to various types of typical Internet connections, Ethernet connections, intranet connections, public switched telephone network (PTSN) connections, and proprietary network connections.

In various embodiments, the subscriber database includes portions that are accessible by the subscriber, portions that are accessible by service providers approved by that subscriber, portions that are accessible for other service providers not yet approved, and portions that are used by the broker service to attend to the various needs of the subscribers. Other accesses are contemplated and the present system is not limited to those mentioned, as they are used to demonstrate the system. Further examples of such embodiments are provided in this disclosure after discussion of the other aspects of the system 100.

In various embodiments, the broker service 106 is remote from the property or properties being serviced. This provides the broker service 106 an ability to be located at one or more locations independent of the property or properties. The broker service 106 can "follow" a subscriber as they move from location to location, whether in a single property or across multiple properties. This is a great advantage over prior art systems using a single control feature, such as alarm systems which use a single alarm panel for a single location. Therefore, the present system allows for a subscriber to use and benefit from his or her preferences and programming across a vast array of locations, whether intra-property or inter-property.

Property Communications Nodes (PCNs)

Figure 2:
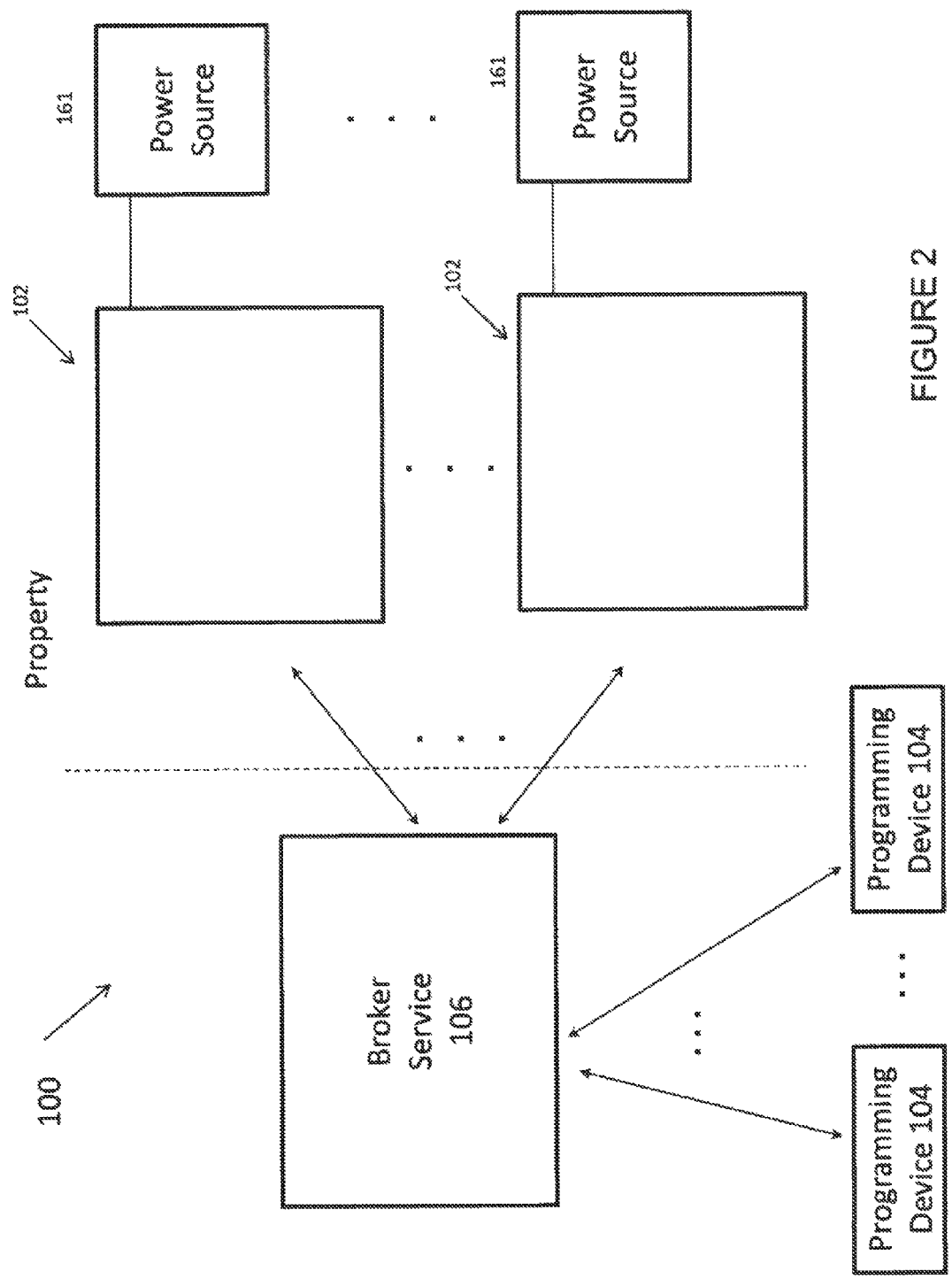

The PCNs 102 that can be used to provide bidirectional communications to subscribers at one or more properties can vary. In various embodiments, each PCN 102 is adapted to communicate with the broker service 106. Consequently, one advantage of the present system is the ability for PCNs to individually and independently conduct bidirectional communications with the broker service 106. In various embodiments, each PCN 102 includes a connection to the power source and is located at the property, as demonstrated in FIG. 2. The PCNs 102 can be used in a multitude of ways that provide programmable, controlled, bidirectional communications with the person or persons at the property for a multitude of new applications. For example, in one embodiment, the PCNs include the electrical switches shown in U.S. Pat. No. 6,894,609 (the 609 Patent) and door lock mechanisms in U.S. Pat. No. 6,967,562 (the '562 Patent), which have been incorporated herein by reference. It is understood that their use in the description is intended to demonstrate the present subject matter, but not in a limited or exclusive or exhaustive sense, and that other PCNs may be used without departing from the scope of the present subject matter. Some of those additional PCN designs are demonstrated by this disclosure as set forth herein.

Figure 3:
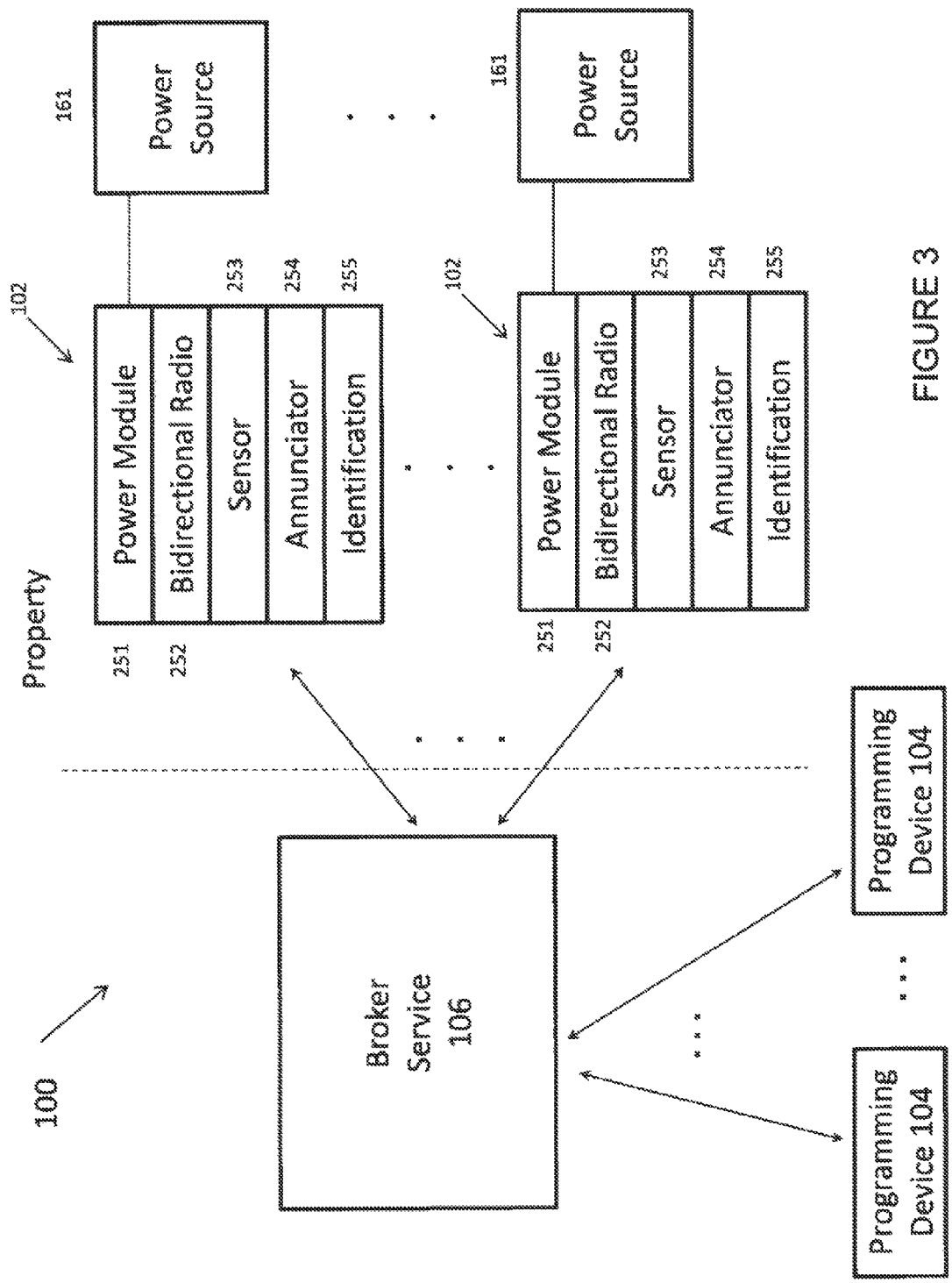

FIG. 3 demonstrates the system 100 according to various embodiments of the present subject matter. The PCNs 102 demonstrated provide a power module 251 which includes circuits for connection to power source 161, such as a typical electrical service. Such circuits may include various features such as a backup power feature that allows the PCN 102 to remain powered for at least a while should the electrical service fail. In some embodiments, a rechargeable battery is maintained at a desired level of charge to function to communicate with the broker service 106 should the power system fail, which is common in typical emergency situations (such as power system failures due to a lightning storm, heat wave, blizzard, tornado, hurricane, or earthquake, for example). In this way, the PCN 102 can provide crucial communications for the disabled, elderly, injured, or young person at a property during such emergency.

PCN 102 also includes a bidirectional radio 252 for communications to the broker service 106. The PCN may employ any number of radio options without departing from the scope of the present subject matter. In various embodiments, the radio 252 is a cellular device that can be connected to the broker service 106 via existing cellular infrastructure. In various embodiments radio 252 is a packet radio device that can communicate with a variety of packet interfaces. In various embodiments, radio 252 is WiFi compatible for internet connections to the broker service 106. In various embodiments, radio 252 is a software radio that is configurable for a plurality of wireless frequencies and/or protocols. In various embodiments, the radio 252 is programmed by an installer upon placement of the PCN 102 at the property. In various embodiments, the subscriber at the property can choose a communication protocol. In various embodiments, the software radio can automatically detect wireless radio communication options available to it and provide a number of options for the subscriber. In various embodiments the software radio can automatically detect wireless radio communication options and select at least an initial service for communications. The subscriber can select another wireless option using programming device 104. In other embodiments, the broker service 106 already contains the subscriber's connection preferences and automatically determines the most preferential connection and programs that into the radio 252. Thus, a number of communication options are possible without departing from the present teachings.

PCN 102 in FIG. 3 also includes at least one sensor 253. The sensor can be any number of possible sensors. In one preferred mode, the sensor is a microphone which can be connected to a microprocessor, microcontroller, digital signal processor, or other digital electronics to accept the sound signal received and process that. For example, a voice recognition feature can be programmed that recognizes the subscriber's voice, the subscriber's children's voices, and/or the voices of select visitors (such as extended family members, the family babysitter, and friends to name a few). This allows for communications from the PCN 102 directly to the rest of the network based on voice recognition and/or voice prompt recognition. Such a system can be deployed, for example, at the residence of an elderly person and allow him or her to automatically call for help by merely stating a known help request sequence. The microphone can be programmed for any number of different tasks including, but not limited to, glass break detection, tone detection (such as a dual tone multi-function or touch tone), or special programming (such as detection of an audio alarm from a subscriber's ventilator or other device). The microphone can also be used for typical voice communications, such as speakerphone communications. The number of possibilities is virtually unlimited.

In various embodiments, the sensor includes a motion detector. A motion detector can be useful for monitoring health and wellness of the elderly. It can also be used for basic security features. It is also possible to use the motion detector to sense when children arrive from school or when the cleaning service enters the property. Therefore, a rich and diverse array of one or more sensors can be used without departing from the scope of the present subject matter.

The PCN 102 of FIG. 3 also includes an annunciator 254. In various embodiments, the annunciator is a speaker. In various embodiments, the annunciator is a video screen or monitor. Other annunciators are possible without departing from the scope of the present subject matter. The annunciator 254 provides a means for distributing content in the property (of course, based on preferences established by the subscriber). For example, in the application for medical reminders, the annunciator may be a speaker which is used to play a message to the occupant to make sure that she takes her medication. In various embodiments, the annunciator can be a video screen and in a chat application, the screen can be used in conjunction with a speaker, a microphone and a video camera that allows the subscriber to have the ability to teleconference in any room having a PCN so equipped. Such teleconferencing can be conducted with others' PCNs or with any business or home having teleconference equipment. Internet teleconferencing with Skype™ or other such conferencing services/software can be easily conducted using the present system. The whole system can be combined with other features to provide a new communication mode not possible in current technologies. For example, assume that the property is equipped with multiple PCNs that each include a motion detector, microphone, speaker, video screen and camera. Such a system could afford the subscriber to move from room to room (or even from inside to outside) and seamlessly conduct a videoconference as the person moves around the property. The motion detector could be used to change PCNs as a person moves from one location at the property to the next one. The microphone and camera can "follow" the person as she moves from one place in the property to another. Of course, some of these functions could be performed with fewer components. It is understood that the microphone could be used to detect when the person moves from one room to another, so a motion detector is not absolutely necessary in some applications. Similarly, the video camera can be used to detect motion in a room. These sensors can also be used in conjunction to provide a seamless handoff of communications from one PCN 102 to the next. It is also possible that certain locations can be specially programmed to control the communications from one PCN 102 to the other. For example, a PCN 102 in a home can be programmed to block video signals from the property unless the communication is to a select desired other location or person. Such programming can be provided via the programming device 104, via PCN 102 (such as with a control switch, software switch, or some programmable feature), via the broker service 106, or all of these. The PCN 102 could be programmed to mute the sound from a microphone unless a communication is unmuted by the person at the property to limit sounds transmitted to another PCN 102 or location. Thus, such a system affords the subscriber a great deal of programmable options that can be used in a multitude of applications.

FIG. 3 also shows PCN 102 with an identification module 255. The actual identification can vary. For example, for fixed PCNs at a location, the identification module 255 can contain at least some of the following parameters: type of location, subscriber identity, PCN location code, PCN identity, and/or special information about the subscriber or property. For example, one variation of the possible information in the identification module is:

a. PCN Ser. No. 10223721
 b. Battery Backup? Yes
 c. Address 78421
 d. Subscriber 203389
 e. Medical Code 37

This example provides information in the PCN 102 that can be coded or not as desired in any deployment. For example, the information contained in the Address storage is a number "78421" that can be correlated to the proper address of the PCN 102 by the broker service 106. It is also possible to directly code the address into the PCN identification module as well. This PCN example also includes a subscriber code and medical code to afford additional privacy to the subscriber; however, they too could also be entered into the device directly. Other special features could be encoded into the identification module. For example, a workplace with hazardous materials could have a code identifying that fact and could even have information about the exact nature of the hazardous materials.

The identification information provides additional programmability options for the subscriber that can add great value to a particular application. For example, in the case of a power outage from a natural disaster the PCNs 102 deployed at a property can continue transmitting information and identification of where that information is coming from and the subscriber can continue to obtain warning information from any emergency service deploying messages to the PCN 102. That natural disaster information or warning can be delivered to any PCN 102 on the network. So for example, if the subscriber is not at the location experiencing the disaster, the broker service can send such information to the subscriber (or persons/places they designate) via any mechanism described herein (for example, PCN-to-PCN communications either directly or using the broker service, email, text messaging, fax, call, cellular phone messaging, to name a few). For example, the PCN 102 can transmit a code when a power outage occurs at a home of a person on a ventilator. That code can be programmably sent to the broker service for dissemination to emergency personnel. The code can also be sent to a monitoring station for dispatch of emergency personnel. The code can also be sent to a loved one as a first line of response in matters of less urgency. Consequently, even if the occupant were unable to communicate via the microphone or other operation of the PCN, the PCN itself can provide information identifying the person, place or thing of interest in any sensing event. For even more communications redundancy in case of outages or temporary loss of communications, the wireless radio 252 can be programmed to make different emergency transmissions to different radio services as available and as needed. This raises the overall intelligence of the interactive communication network greatly and provides adaptive alerts to respond to any number of conditions and applications. In various embodiments, a messaging feature for national disaster or national emergency can be conducted from connections to a single network messaging from FEME (the Federal Emergency Management Agency). For example, FEMA has an IPAWS service (Integrated Public Alert and Warning System) that can be deployed using PCNs 106 and the broker service 106. (Or any system mandated by Congress.) Indeed, the subscriber can even program how he or she would like to receive such information. This is a great advantage over typical deployment mechanisms such as an audible horn or other radio warning system.

Figure 4:
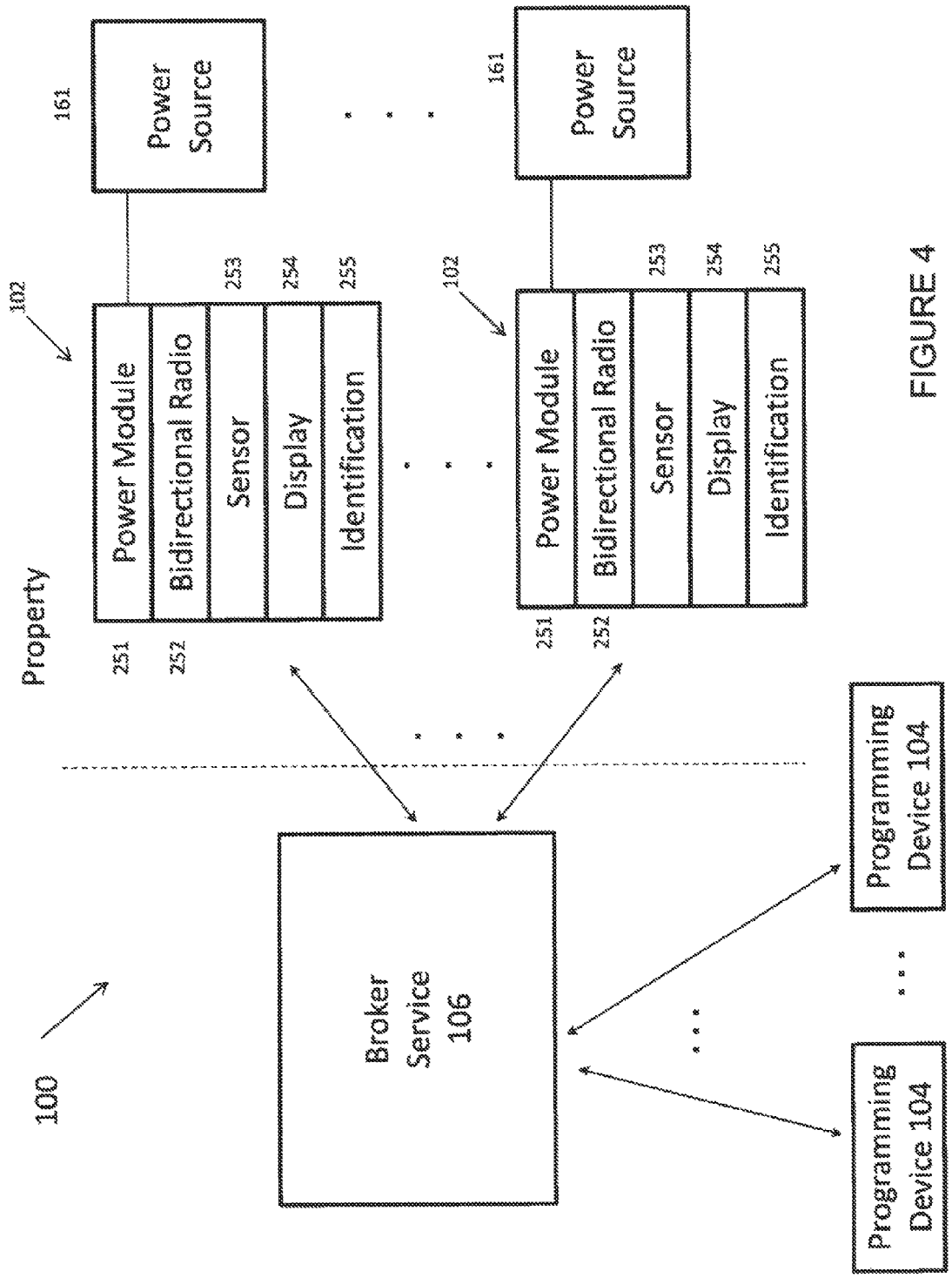

FIG. 4 shows a network similar to that of FIG. 3, but with a display as the annunciator according to various embodiments of the present subject matter. It is understood that the display 254 can be built into the PCN 102, wired to the PCN, or wirelessly in communication with one or more PCNs. Any number of video and audio devices, including, but not limited to, screens, monitors, cell phones, smart phones, laptop computers, desktop computers, televisions, iPads, and/or iPods can be in communication with the PCN for video and audio applications.

A PCN 102 functions as a user interface that can request content, receive content (live streaming, downloaded feed or high density packet, for example), interact with content, and provide content, in various embodiments. PCNs 102 communicate directly with a broker service 106 via wireless communication, in an embodiment. The user can control settings using verbal commands to a microphone or other sensor at the PCN 102, in an embodiment. In various embodiments, the user receives audible information from the broker service at a speaker of the PCN 102. Verbal commands can be used both at the PCN and/or at the broker service side.

Programming Devices

The programming devices 104 can provide instructions and parameters for the broker service 106 to control communications with the PCNs 102. The programming devices 104 can perform the programming over any number of networks, including, wired or wireless networks. The wired networks include, but are not limited to, an attached computer, a local area network, an Internet connected network, a public switched telephone network (PTSN), and combinations thereof. The wireless networks include, but are not limited to, cellular, WiFi, Bluetooth™, and combinations thereof. Combinations of wired and wireless networks can be used to perform programming. The typical application affords a subscriber the ability to program preferences in an account with the broker service 106. The programming devices 104 can also be used with certain PCNs where appropriate to control communications by the PCNs.

Some programming devices 104 include, but are not limited to cell phones, smart phones, laptop computers, desktop computers, televisions, iPads, iPods, TiVo® systems, Wii® systems, Playstation systems, iPods®, and/or iPhones® to name only some. The programming devices 104 can access a programming interface of the broker service 106 from a variety of approaches, including but not limited to: a personal contact that can assist the subscriber to programming their preferences; software running on the programming device 104, such as an applet; a browser-based access point to the subscriber's account on the broker service 106; and/or an access from a PCN 102 programmed to provide contact with the broker service 104 for the subscriber. Other types of user communication can be used by the programming devices 104 to control settings and receive notices from the system, such as e-mail, text messages, Twitter®, Facebook®, LinkedIn®, and other social networking websites, without departing from the scope of the present subject matter. In various embodiments, the programming device 104 may also be used as a display 254 or in conjunction with that display. Other contact options are possible without departing from the scope of the present subject matter.

Programming devices 104 can be used by subscribers. They can also be used by service providers who are providing services to the subscriber. For example, in an example where security monitoring is provided, a security company may supply codes to the subscriber to use in case of an emergency via the system to alert the security company to a need. For instance, suppose the security company receives an alert from a property that a break in has occurred. The security company can use its programming device 104 as an apparatus to monitor other locations of the property that were pre-approved by the subscriber in such emergencies. For example, the security service may have access to a camera fixed on the driveway to see if a vehicle is parked there or to tell when police have arrived. Thus, a number of uses by a trusted service provider of the programming device 104 can be envisioned by the present system and can be controlled by the subscriber.

Figure 5:
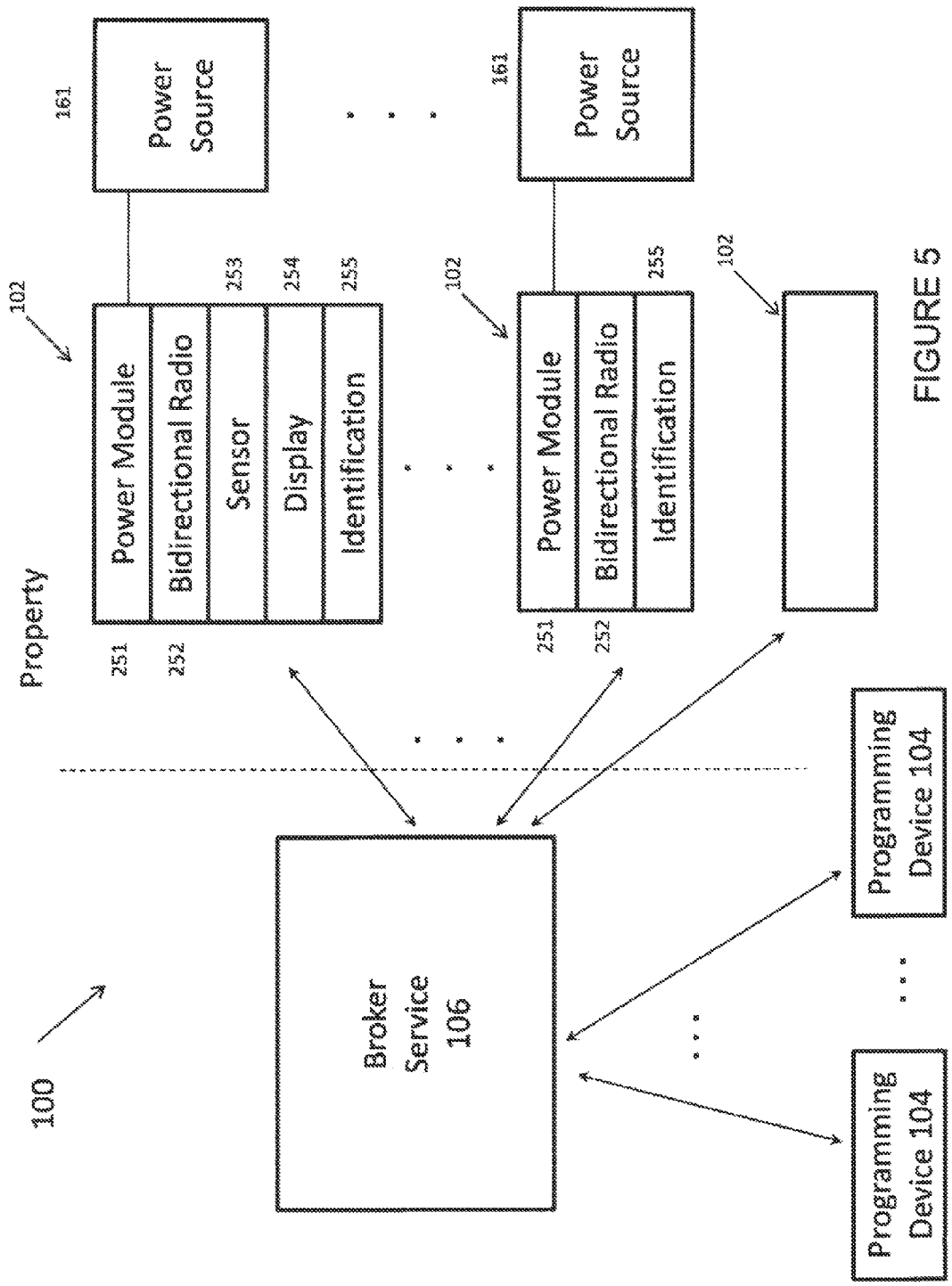

FIG. 5 shows a diversity of communications options that can occur between the broker service 106 and different types of PCNs 102. The PCNs can vary in aspects, such as sensors, communications, annunciators, and connection to external power systems. Other variations are possible, and this example is provided to show that the devices have a rich interconnectivity that can be exploited for different applications.

Figure 6:
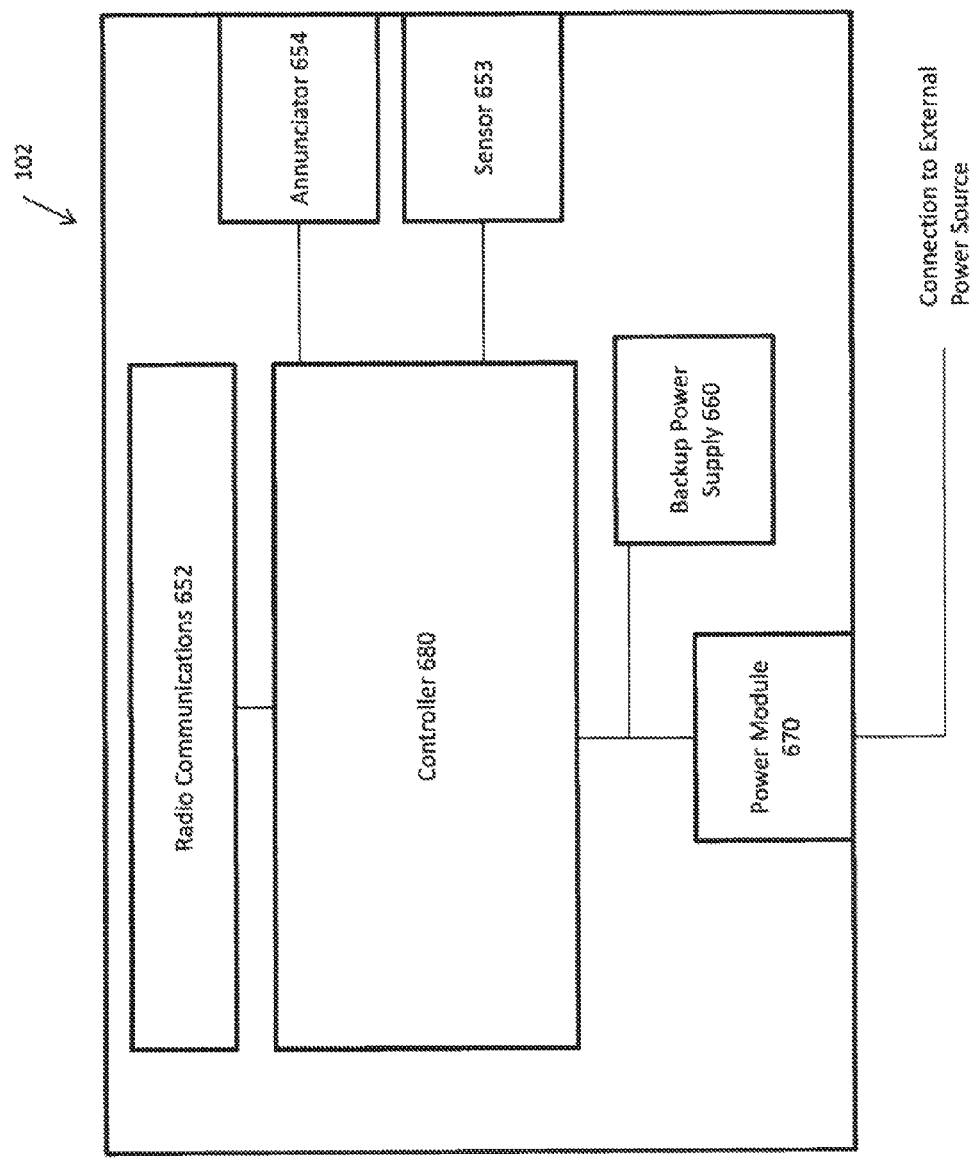
FIGS. 6 and 7 show different embodiments of some property communication nodes according to various embodiments of the present subject matter.
Figure 7:
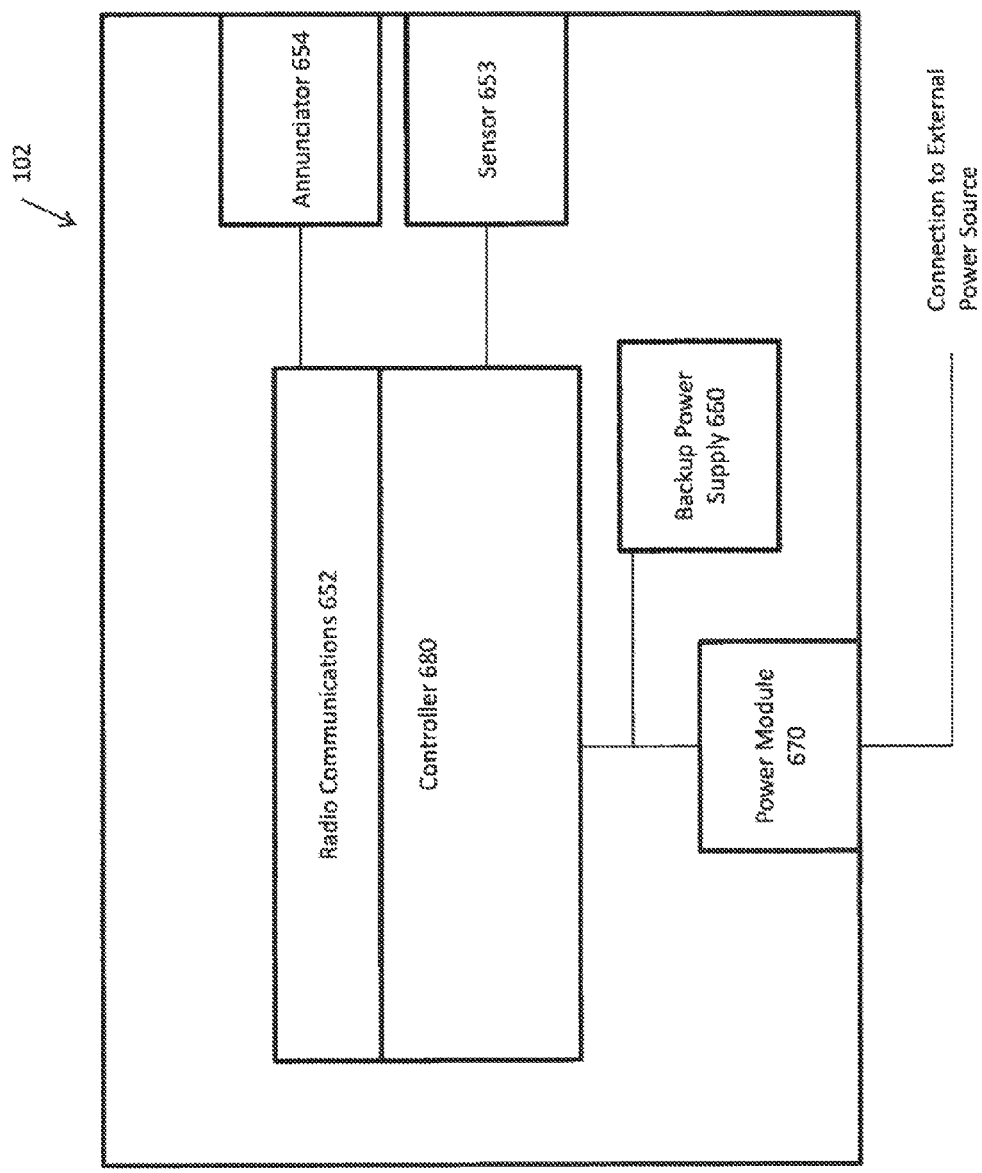

FIG. 6 is a block diagram showing different functional blocks of one type of PCN according to one embodiment of the present subject matter. This particular PCN 102 includes a controller 680, a radio device 652, a backup power supply 660, a power module 670, an annunciator 654, and a sensor 653. In various applications, the controller 680 is a microprocessor, digital signal processor, microcontroller, dedicated ASIC, combinational logic, or other type of digital device. The radio communications can be integrated into a processor in some embodiments, such as that shown in FIG. 7.

In various embodiments, the PCN 102 includes a battery backup including a flag or light to signal low power when the battery was getting low. In various embodiments, the backup provides a flag to the broker service that can be programmed to: (1) send a message to emergency aid if the power goes low (e.g., elderly person who has no power, or person on a ventilator that has lost power); or (2) send a message to a friend or family member programmed into the device or the broker service if the power goes low (e.g., elderly person who has no power, or person on a ventilator that has lost power); (3) provide selective access to inquiries by a list of authorized inquirers (e.g., daughter logs into system because she has not heard from her mother who is elderly and daughter has access to system).

Figure 11:
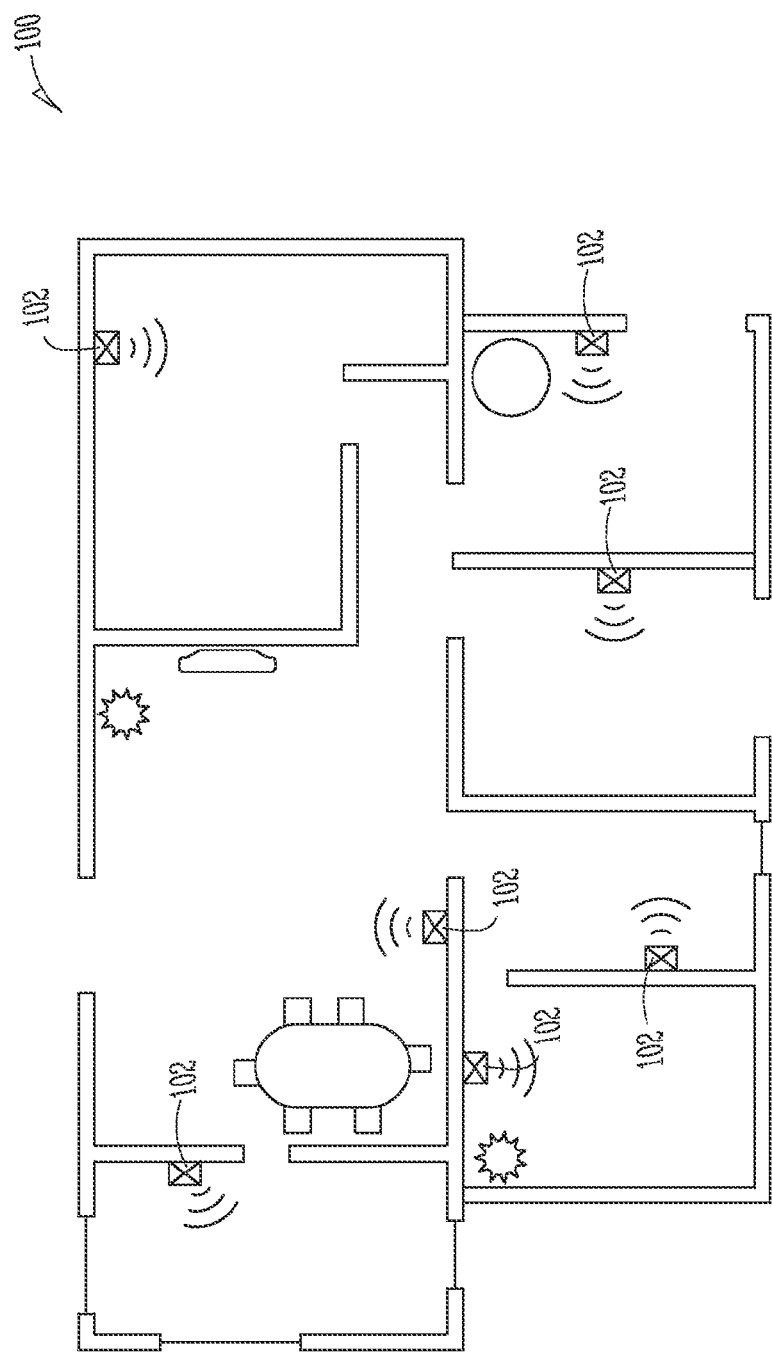
FIG. 11 shows one example of deployment of property communication nodes.

FIG. 11 shows an example of a dwelling with a plurality of PCNs 102 deployed in various locations. The depicted embodiment illustrates a residence, but the present subject matter is not limited to residences. Additional examples of properties include, but are not limited to, a business, office, factory, cabin, cottage or garage. Other types of properties can be serviced without departing from the scope of the present subject matter. The location of PCNs is unlimited. PCNs can be integrated into a variety of home and office hardware, such as switches, outlets, appliances and other devices. For example, a PCN 102 can be integrated into a refrigerator or other kitchen appliance. PCNs can be integrated into a security camera or other such device. PCNs can be deployed outside of a structure and over grounds. PCNs 102 can be set up in warehouses and in parking lots. The applications are unlimited. The detectors housed with the PCNs 102 track the user and can transfer communications using a handshaking protocol to provide an interactive communication system that follows the user throughout their property, according to various embodiments. In a system using a plurality of PCNs 102, the PCNs 102 can programmably contact other PCNs 102, programmably broadcast from a single PCN, multiple PCNs, or all PCNs. The PCNs can perform select addressed transmissions to each other at one property or between properties.

Figure 12:
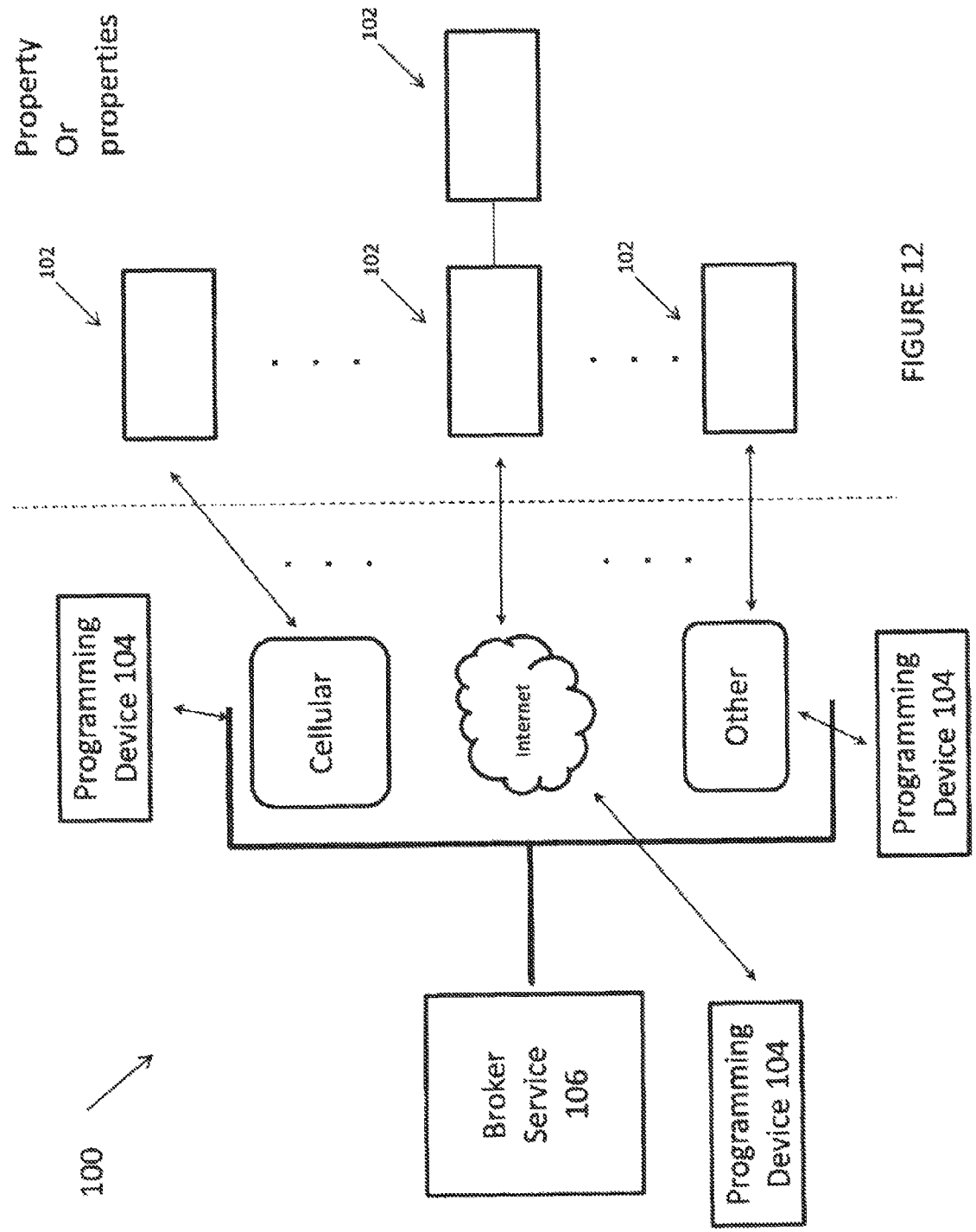

FIG. 12 shows a diversity of communication connections for the broker service, the programming devices 104, and the PCNs 102. The present system allows a subscriber to use a variety of communication networks to stay in touch at a property or properties. This allows for seamless communications from different places a person resides, from their home to their office and even their loading dock. The communication options are unlimited.

The broker service is shown as a single block in the attached drawings but it is expected that the broker service can take place over a number of computers or servers or services. For example, the broker service can use one set of addresses/communications for high priority communications such as emergency or other such services. The broker service can use more traditional and slower access options for more routine communications or low priority communications. The broker service can be deployed in a cloud computing environment or other distributed processing environment. The broker service can also interface with other service providers to provide services for its subscriber base.

The broker service 106 can include personalized or programmable brokers that provide content, such as Netflix or Google® in various applications. Other examples of a broker service 106 include interactive services provided by private security companies, health care facilities, medical professional networks, advertising and sales, and connections to family and friends. Such services are rich and include, but are not limited to, visual, audio, and data services. PCNs 102 can communicate with multiple services via the broker service to perform multiple functions, in various embodiments.

It is understood that the PCNs 102 can aid or assist other functions, such as home security systems. In one application a security system panel can also act as a PCN or interface to a PCN. Thus, the present system can supplement current more primitive systems.

In the communications stated in this application it is understood that the communications can include a repeater, gateway, switch, router, bridge or network interface, and that the examples given herein are intended to demonstrate only some of the optional configurations.

The interactive property communication system provides wireless connectivity both intra-property and inter-property, in various embodiments. In various embodiments, intra-property communication among PCNs 102 can be facilitated by modulating a signal on the electrical power network throughout the home or building as described in the '609 patent that has previously been incorporated by reference.

In various embodiments, the interactive property communication system connects one or more PCNs directly to the Internet, or to the Internet via the broker service. The geographical range of communication can be extended by linking a wall mounted PCN with a second device (repeater or intermediate node) that is coupled to a long distance communication network, such as by using a short range network such as BLUETOOTH®, HomeRF™, wireless LAN (WLAN), or other personal wireless networking technology to connect to the second device, as described in the '609 patent that has previously been incorporated by reference. As further stated in the '609 patent, the range may be extended by coupling a BLUETOOTH® transceiver with a cellular telephone network, a narrow band personal communication systems ("PCS") network, a CELLEMETRY® network, a narrow band trunk radio network or other type of wired or wireless communication network. The interactive property communication system can be connected to the United States Government's Integrated Public Alert and Warning System (IPAWS), in one application. In one embodiment, the interactive property communication system is connected to a property security system broker to provide security for the property.

In various applications, algorithms at the broker service include voice recognition algorithms to process information from the property to provide programmable, automated alerts to response agencies for a particular detected emergency. Thus, the voice detection features can be at the property or at the broker or both.

In various embodiments, the interactive property communication system includes hardware, software and related systems configured for monitoring and reporting of operability, continuous or timely status alerts, and reporting to alert the user or users and to allow users to modify usage or have knowledge of loss of functionality. Thus, malfunction or abnormality is verbally reported to the user on the PCN 102, via a video monitor 302 on or connected to the PCN 102, transmitted to their account on the broker service, and/or sent to their personal computer and cell phone or other personal device, in various embodiments.

The present system has many uses, including but not limited to some of which are set forth herein to demonstrate the rich programmability and applications of the present interactive communications system.

Improved Messaging System

The present system affords the users of PCNs to programmably control communications with friends and family in a way not possible with present telephone systems. For example, suppose a family wants to establish communications among family members. Each member can exchange PCN contact information and can then program the broker service with communication options and preferences. For example, suppose the mother of the family wants to limit calls outside of 9 a.m.-8 p.m. every day to ones where it is an emergency. She can program an option in the broker service to filter family calls that are outside of the 9 a.m. to 8 p.m. range to only ones where the caller has indicated an urgency or emergency. The prompts and answers needed to decide what is urgent can be programmed as well.

The system can also be programmed to recognize the mother's voice and perhaps a special spoken sequence to perform calling. For example, the system can be programmed to recognize the mother saying "I need help" or "I need help quickly" and take appropriate action as programmed by the system. For example, upon receipt of such a verbal command, the system can be programmed to call her daughter, text her, and/or simply open a communications pathway so that she can speak directly to her daughter at her PCN. This provides an enormous service since the daughter could be at any location fitted with a PCN and be in almost immediate contact with her mother. For example, assume the daughter is on travel in another city. She could get a message on a PCN in her hotel room or she could have immediate voice and/or visual contact with her mother due to her emergency.

The system is good for emergencies, but is also exceptionally good for less urgent communications. For example, a feature that can be easily implemented is an "I am free to talk" feature, whereby the person sets a status using her programming device 104 or a PCN 102 so equipped to receive the status, that he or she is free to talk. (This could be done by any number of programming options, including, but not limited to a code entry, checking a box on an interactive device screen, or merely a verbal command to the programming device 104 or PCN 102.) The broker service now knows that person is free to talk and can be programmed to make a connection with other friends and family that have also programmed their systems as such. Such programming could result in a voice or voice-and-video conference almost immediately with the other family member. Indeed, the whole family could be joined by the broker service if all of them were available or willing to chat. This feature brings a whole new dynamic to interpersonal communications. It lessens the divide in location between people who want to communicate and makes personal communications a great deal easier than logging into a website or using conventional calling and/or teleconferencing abilities.

The broker service can add another dynamic to the communications. It can have a messaging feature that notes to a select list of persons that certain members of the family are online and welcome an additional party to the contact. This feature can also be deactivated to avoid intrusions to private communications. Thus, the programmability and messaging features of the present service in combination with the inter-property and intra-property communications add a dynamic that cannot be experienced with traditional services.

The broker service features can also be used for social networking to greatly expand the ability for users to connect. The "free to talk" feature can be used by members of a trusted group of friends and family on a social networking site, including, but not limited to, social networking sites such as Facebook, Twitter, MySpace, LinkedIn, to name a few. The broker service 106 can be interfaced with such social networking sites to populate contact information, to globally establish communications from the PCNs under the programmable control of the subscriber, and to establish a whole new genre of intercommunications based on personal status and settings that may be detached from the traditional browser-based communication approach of such social networking sites. The possibilities are unbounded, but some are provided to demonstrate the richness of the present system. For example, a social network could be used to establish a list of wanted or trusted friends that could arrange a multiperson chat session using the broker service, the social networking site and the PCNs of the present subject matter. For example, the present system could go from an online chat to a PCN discussion merely by an instruction sent to the broker service and/or the social networking site. As such, the present system could have a software feature that converts all on the network chat to a verbal discussion or verbal teleconference, as desired.

Another feature is that people who have met on the networking site and wish to conduct more personal discussions or teleconferencing can provide each other with a secret code or link to provide that person an ability to conference or teleconference without giving out a phone number, an address or other personal information. That provides the persons who are still new to a potential relationship the ability to meet at their own locations (a safe ground to meet electronically), and avoid giving sensitive information to the intended other person until more of a trusted relationship can be established. Such a system could be a single use approach so that any link or code used is useful only for a single communication, giving the parties the ability to more abruptly terminate contact if desired. Of course, due to the sensitive nature of such potential, a parental approval feature can be employed to limit or block entirely the ability to perform such communications. A monitor mode can also be established to allow a third party the ability to chaperone the discussions, for example. As can be seen from the present discussion, any number of telecommunications options are possible with the present system and those given herein are intended to demonstrate the system and not in a limited or exclusive sense.

The present system can also be used to define what communications occur and where in any given property. For example, a single room could be designated as a room for audio and video communications, and such communications could be limited to blocked from any other location at the property. This approach redefines a "chat room" to be a location at the property where chatting is permitted, not unlike having an electronic meeting hall where all associated with the discussion could freely discuss and teleconference or televideoconference. Again, such programming options are unlimited and this example is provided to demonstrate new aspects of the new system.

News, Entertainment, Education, and Other Content

In various embodiments, the present system can be programmed to distribute content such as news, entertainment, education, special programming, requested programming, and any other content to the subscriber. For example, the system can include programming at the broker service to indicate which news sources and/or which news topics the subscriber wishes to receive. The subscriber of such a system could be doing a mundane household chore, such as laundry, and receive a notification from the PCN that a news story on the presidential election is available and ready for listening, viewing, or both of them. In various embodiments the PCN is adapted to provide a voice prompt to the subscriber, such as "Do You Want to Hear a News Story?" or even "Do You Want News About the Election?" The subscriber can program his or her interface to play it upon an acceptance response or to automatically play certain messages due to their urgency or importance. The system can also be programmed to pause or skip a news story upon instruction of the subscriber. This provides a new way for the subscriber to receive news and such receipt can be optional or not, as the subscriber wishes to program the system. Such programming can be extended to entertainment and other such communications. For example, education or learning at home can be performed using the present system.

The broker service can be programmed to play emergency information to the subscriber that is dependent on the geographical location of the subscriber. Therefore, a person visiting an area frequently experiencing earthquakes may receive instant warning and emergency response information from the local emergency information network. In the U.S. the system may be connected to FEMA and may receive messages from IPAWS. Other emergency communications and services are possible. The subscriber can also elect to receive emergency messages from other locations, including, but not limited to, the locations of loved ones, the locations of other properties of the subscriber, to name a few. The scope of information available to the subscriber is not limited and may be programmable to only those things of interest.

This feature also allows the broker service to interface with other news and entertainment services to provide the subscriber content based on their preferences.

Advertising-to-the-Person-at-a-Property

The present system can also be used to control the content of what the subscriber hears/sees from his or her PCN for the purpose of advertising. This feature allows the subscriber the ability to eliminate unwanted advertising or to even solicit for certain types of wanted advertising (e.g., "Send offers for sales of new hybrid electric cars."). Such as system can also be connected to other websites such as eBay (e.g., "Notify for sales concerning antique china.").

The present system allows the subscriber to control only what sales items that he or she wants. The subscriber can select one or more of: retailers, product categories, brands, sale or discounted items, vendors, and a host of other potential parameters. The subscriber may access a selection menu or other interface using the PCN 102 or the programming device 104 (among other options) in communication with the broker service 106. Other possibilities are that the subscriber can sign up for a service that interfaces with the broker service to provide selections that may be selected and thereby get only desired solicitations or offers.

The subscriber can select notification parameters as well. For example, if the desired car is offered for sale they can program the system to notify them immediately. They can also review the product visually for PCNs so equipped or using their own monitor. They can then order the product or service and buy it immediately by selection directly through the PCN 102 or programming device 104.

In one embodiment, the subscriber can choose how many notifications the system can make and after a predetermined number the system can put the message of the sale item or service to be stored on the broker service 106 or the PCN 102 or sent via messaging or email, or any number of other communication options, as programmed by the buyer/subscriber.

The subscriber can also select a chat option to discuss a purchase with a vendor/retailer or other seller. The system can be programmed to transfer the buyer's personal and payment information as authorized by the buyer/subscriber to inform the seller of certain information that the seller desires.

The present system allows the subscriber to save time shopping for things and from a multiplicity of undesired offers by specifying his or her own interest and limiting communications to only the ones desired by the subscriber. This also makes the subscriber's purchase decision more efficient. It allows the subscriber/buyer to purchase, select a shipping/pickup option, discuss the purchase, and perhaps close the buy quickly. It also saves the cost and effort of vendors and retailers in generating catalogues and other sales literature that will never achieve sales.

Again, the possibilities are unlimited and the examples given herein are intended to demonstrate some of the rich programmability and advantages of the present system.

Advertising to the System

Broker Service 106 of System 100 can be used to establish business and/or other distribution relationships with a variety of entities, including, but not limited to various sellers, retailers, wholesalers, distributors, merchants, creators, Broker Service 106 itself, and various partners and/or suppliers and combinations thereof. For the purposes of this document, these individuals will be referenced as "Third Party Vendors". The Third Party Vendors can be vendors or representatives of a variety of goods and services, including, but not limited to, general and specific: products, services, commodities, brands, articles, single, multiple and/or continuous delivery of requested subscription, information or content in various forms and presentations, such as but not limited to programs, travel, lodging, entertainment, dining, news, sports and education. Such goods and services shall be referenced as with the intent and design that the person at the property (abbreviated as "PAP") will be able to receive requested and specific notification and view and select on PAP's PCN(s) 102, Programming Device(s) 104 and/or any other object of connectivity supported by the System 100 which Third Party Vendor's goods and services offerings are of interest and at, but not limited to, what desired pricing, terms and conditions if necessary. Further, the PAP selects notification specifications, and/or other parameters on how the PAP wishes to be notified by and/or through Broker Service 106 Third Party Vendors when PAP's requested and/or preferred terms and conditions, etc. are met by Broker Service 106 goods and services offerings and/or selected Third Party Vendor's goods and services offerings.

Broker Service 106 will specify to Third Party Vendors what web site and/or other forms of presentation and/or connectivity Third Party Vendors will present to Broker Service 106, allowing a PAP and/or subscriber of Broker Service 106 to utilize one or more PCNs 102, Programming Devices 104 and/or any other object of connectivity supported by the System 100 to view all of the PAP requested Third Party Vendor partners and their goods and services offerings provided using Broker Service 106. The PAP can connect to and/or through the Broker Service 106 to the Third Party Vendors' customized interface via Broker Service 106 and/or to the Third Party Vendors' website of goods and services offerings using existing or modified Third Party Vendors' buyer/consumer website(s) of offerings located at designated individual Third Party Vendors' sites.

The PAP can register on a Broker Service 106 customized master form residing on the Broker Service 106 that shall have pertinent Broker Service 106 required and PAP requested terms and conditions for all Broker Service 106 authorized and PAP-selected Third Party Vendors. Some of the required information that the PAP would enter on the Broker Service 106 master form may include, but not be limited to one or more of: name of Third Party Vendors, Third Party Vendors' goods and services catalog identity number, goods and services description, model, size, color, pricing, discount and/or range request amounts if necessary, number desired, valid date range of the PAP's interest, the PAP's notification requirements used by Third Party Vendors performing announcements of the PAP's successful match(es) on the PAP's PCN 102, Programming Devices 104 and any other object of connectivity supported by the System 100.

Parameters that can be used to specify an interest notification to PAP(s) include, but are not limited to, immediate, one or more days of a week, between certain hours Third Party Vendors' announcement(s) are permitted, daylight savings time observed—yes or no, number of announcements per day and for what duration and in what received formats such as, but not limited to, text, email, audio and/or visual presentations on the PAP's PCN 102, Programming Devices 104 and any other object of connectivity supported by the System 100. A PAP can use Broker Service 106 to control Third Party Vendors via the PAP's PCN 102, programming devices 104 and any other object of connectivity supported by the System 100 include, but are not limited to, stopping announcements, to control their duration as specified by the PAP, whether the notification should expire, to store the message to be retrieved at a later time, and a variety of other messaging controls. If the PAP desires message(s) to be stored, then a PCN 102 may display on a designated page or screen on a PAP's monitor Annunciator 254 or PCN 102 face-plate, programming devices 104 and any other object of connectivity supported by the System 100 a graphic symbol indicating a message(s) has been automatically stored on the PAP's selected 102(s), Programming Device(s) 104, the PAP's personal member account page on the Broker Service 106 and/or any other object of connectivity supported by the System 100.

In various embodiments, a PAP may log into or sign on to PAP's private or personal account on Broker Service 106 by using PAP's PCN(s) 102, Programming Device(s) 104 and/or any other object of connectivity supported by the System 100 and convey or transfer PAP's own content such as, but not limited to, text, graphics, pictures, audio, video, information, instructions, messaging, programs or any combinations thereof to PAP's personal and private account data base on Broker Service 106 for subsequent selection, transfer and/or retransfer of any of a PAP's selected and owned content resident or stored on a PAP's account data base on Broker Service 106 to a PAP's owned and managed PCN(s) 102, Programming Device(s) 104 and/or any other object of connectivity supported by the System 100. In such case, a PAP already has ownership and manages all other necessary details, but not limited to, such as selected Identification 255 number destinations, date and time ranges, frequencies and all other necessary control commands to control and manage a PAP's own transfer, retransfer, usage and consumption request(s).

Similarly, in various embodiments, a PAP may log into or sign on to PAP's private or personal account on Broker Service 106 by using PAP's PCN(s) 102, Programming Device(s) 104 and/or any other object of connectivity supported by the System 100 to request transfer of a PAP's content such as, but not limited to, text, graphics, pictures, audio, video, information, instructions, messaging, programs or any combinations thereof to another PAP's Interactive Property Communication System's personal and private account data base on Broker Service 106. Broker Service 106 shall forward initiating a PAP's request to other receiving PAPs for their approval. Upon receiving a PAP's approval, the receiving PAP shall then supply Broker Service 106 with receiving device(s) identification number(s) 255, approved dates, times, durations, etc. for intended transfer of content to receiving PAP's specific PCN(s) 102, Programming Device(s) 104 and/or any other object of connectivity supported by the System 100.

In various embodiments, a PAP's PCN(s) 102 may be, but are not required to be, housed in a single fixed unit or multiple fixed units mounted and/or attached to, among other things, a wall, bracket, electrical outlet or electrical switch, or other permanent type attachment. Similarly, in various embodiments, a PAP's PCN 102 may be, but is not required to be, housed in a single fixed unit or multiple fixed units individually mounted on a flexible and/or articulating arm and mounted and/or attached to, but not limited to, a wall, bracket, electrical outlet or electrical switch, or other permanent type attachment allowing the PAP or designee of PAP to use one or more PCN(s) 102, Programming Device(s) 104, the PAP's personal member account page accessible to the Broker Service 106 and/or any other object of connectivity supported by the System 100 to remotely control and have the PCN(s') 102 on-board motor and software to move and articulate the PCN(s') 102 arm to swing, rotate, tilt, extend or retract or any combination thereof the PCN(s) 102 for improvement of, but not limited to, viewing video and/or monitor on annunciator 254, focusing motion detector on sensor 253, ambient light sensor on sensor 253, camera on sensor 253, speaker on annunciator 254 and video monitor annunciator 254 and display 254.

PAP's PCN(s) 102 sensor 253 devices are able to (but are not limited to) perform: capturing, recording and/or for immediately or later processing, transmission and storage or other manipulation operations and/or capabilities of use of the, but not limited to, output captured or recorded by sensor 253 devices such as, but not limited to, types, levels, times, motion, light, darkness, sounds, noises, voice, pictures, images, video, and streaming video. In various embodiments PAP's PCN(s) 102 annunciator and/or display 254 may contain, but are not limited to, an audible or audio transducer, sound generator, piezo and/or speaker that is capable of generating live or stored content to play at PAP's or PAP's designees selected later dates and times sounds, voice, text to speech, messages, audible capabilities, video output that is capable of generating live, stored or memory to play or re-play presentations of, but not limited to, pictures, graphics and streaming video, programs, content from Third Party Vendors and their partners, operating functions, status and controls of PCN(s) 102 and identification 255 which may contain, but not limited to identification of: zone, area, location, ownership identification management control, associated PAP and or other occupants, where permanent or transient personal coding information and personal identity characteristics, personal, medical and valuable personal information and history, emergency contact information for designated people, operating, history and system control identification or further sub-divided of operating and/or bi-directional communications system(s) identification and location, physical street, city, state, zip code, latitude and longitude, global positioning system (GPS) data gathering and/or generating and receiving location and other information and location identity, permanent and temporary assigned user pin numbers or codes of certain PAP's and other persons approved to operate one or more PCN(s) 102, Programming Device(s) 104, the PAP's personal member account page accessible to the Broker Service 106 and/or any other object of connectivity supported by the System 100 video for immediate or later processing, transmission and storage or other manipulation operations and/or capabilities, Annunciator 254 which may contain, but is not limited to, an audible or audio transducer, sound generator, piezo and/or speaker that is capable of generating live, stored or record for play at later dates and times sounds, voice, text to speech, to name but a few audible capabilities and Identification 255 which may contain, but is not limited to, zone, area, location, ownership identification, PAP and or other occupants, where permanent or transient personal coding information and personal identity characteristics, personal, medical and valuable personal information and history, emergency contact information for designated people, operating, history and system control identification or further divided system(s) identification and location, physical street, city, state, zip code, latitude and longitude, global positioning system—GPS—generating and receiving location information and location identity, permanent and temporary assigned user pin numbers or codes of PAPs and other persons approved to operate one or more PCN(s) 102, Programming Device(s) 102, the PAP's personal member account page on the Broker Service 106 and/or any other object of connectivity supported by the System 100.

The PAP may hear an audio, voice and/or hear and see an audio, voice and visual announcement from a Third Party Vendor through and under the control of the Broker Service 106. The audio or voice/visual announcement may arrive over a speaker and/or video-monitor of a PCN 102 or, including but not limited to, a Programming Device 104, cellular phone and/or any other object of connectivity supported by the System 100.

Such PCN or other device may include a video monitor annunciator 254. However, it is understood that in some embodiments, no video monitor annunciator 254 is necessary. If the PAP is not present at the property when a Third Party Vendor's announcement is played on a PCN's 102 annunciator 254 (e.g., a speaker, video or other annunciator) or other device supported by System 100, in various embodiments, the Third Party Vendor's announcement shall repeat as determined by a PAP's announcement schedule programmed on Broker Service 106. For example, if a PAP has selected that if after Third Party Vendor's first announcement is made and the PAP does not respond (e.g., because they are not present at designated PCN 102(s) or are present at designated PCN 102(s) but wish not to respond), the Broker Service 106 may be programmed to post on a designated page accessible by the PAP's designated PCN 102 monitor 254, PCN 102 without a video monitor annunciator 254, Programming Device 104, Broker Service 106, cellular phone and/or any other object of connectivity supported by the System 100, a graphic symbol or other suitable indication informing PAP that a message has been stored on the PCN 102, Programming Device 104, Broker Service 106, cellular phone and/or any other object of connectivity supported by the System 100.

Further, the PAP while present at the designated PCN(s) 102 may simply issue a short command or manually press a designated command on the PCN(s) 102 that will immediately force the announcement to terminate and be routed to the PAP's queue at the broker service 106 and/or the PAP's PCN(s) 102, Programming Device 104, Broker Service 106, cellular phone and/or any other object of connectivity supported by the System 100 for future retrieval.

In another variation, the PAP upon hearing an announcement may immediately speak a different short verbal command into the designated the PCN(s) 102 microphone sensor 253 or manually press a designated command on the PAP's PCN 102 to cancel the announcement thus avoiding having the announcement go to the PAP's message queue on the broker service 106 and/or the PAP's PCN 102, Programming Device 104, Broker Service 106, cellular phone and/or any other object of connectivity supported by the System 100. Additionally, the PAP will have selected on its notification programming (e.g., a notification form) associated with the Broker Service 106 instructions on how many times the PAP desires incoming announcement(s) is to be played without a response by a PAP before the announcement ceases to sound on the PAP's PCN 102, Programming Device 104 and/or any other object of connectivity supported by system 100. In various embodiments, the Broker Service 106 can be programmed to direct the announcement to PAP's message queue on the Broker Service 106.

A PAP can program an associated PCN 102 (or plurality thereof) and/or an interface at Broker Service 106 to control how inbound communications are handled. In various embodiments, the PAP can control the storage of inbound communications. For example, inbound communications can be stored in a message queue on one or more PCNs 102 and/or on Broker Service 106. The PAP can also program the messaging options to provide alerts. In some embodiments, an alert can be an audio alert. In some embodiments, an alert can be a graphic symbol on a specific page or displayed on a monitor annunciator 254 (if utilized). Such graphical alerts may be by a symbol, such as a message light illuminated on the PCN 102, and by the PAP at any time going to their private customer account at Broker Service 106 to review any and all messages in queue whether from Third Party Vendors, from Broker Service 106 management and any other PAP-authorized user of the Broker Service 106.

The Broker Service 106 can be programmed by a PAP by receiving one or more voice and/or manual commands and converting them into actions performed by the Broker Service 106 and/or System 100. In various embodiments, a PAP can issue a verbal and/or or manual response to an announcement of an offering by a Third Party Vendor. In some embodiments, a voice command is received by a microphone sensor 253 of the PCN. The received voice command can be used to arrange and initiate a voice chat with a representative of a Third Party Vendor. The communication may be to answer questions from the PAP regarding the offering and may communicate information to make a purchase or decline to purchase the offering. In various embodiments, a request to enter into a live two-way conversation can be made with a Third Party Vendor sales and/or customer service agent. In such cases if a monitor annunciator 254 is used, additional information can be viewed, including, but not limited to, product cut sheets, photos, actual item images, video clips on or related to the PAP's desired goods and services, conferencing with other Third Party Vendors associates regarding additional goods and services information such as, but not limited to, transferring information about which store the PAP may purchase and/or pick-up Third Party Vendor's goods and services, and to discuss shipping options. Additionally a camera sensor 253 may be utilized, to allow the PAP to verbally or manually activate a particular PCN (or a plurality of PCNs) 102 camera Sensor 253 and enter into a live full two-way audio-visual session where the PAP can utilize and share visual cues such as, but not limited to, facial, hand and body movements that can more fully convey PAP's thoughts and emotions regarding the contemplated purchase of Third Party Vendor's goods and services. Additionally, in the live two-way full audio-visual session the PAP can more completely communicate such as, but not limited to, demonstrate, illustrate, show, draw diagrams, show actual samples, pictures, etc. to the Third Party Vendors representatives thus more fully articulate the PAP's interest to the Third Party Vendors regarding the pending purchase of the Third Party Vendors goods and services. The PAP can at any time retract or turn off connectivity features such as monitor annunciator 254 and camera sensor 253 by speaking a command or manually selecting the associated controls on the designated PCN(s) 102, which will turn off the desired function at the designated PCN(s) 102.

Should the PAP desire to purchase the Third Party Vendor's goods or services offering, the PAP may speak or manually enter into a PCN's 102 microphone Sensor 253 or monitor Sensor 253 and state to the Third Party Vendor the PAP's code(s), if required by a Third Party Vendor and selected by PAP and registered on PAP's private customer account at Broker Service 106. In this circumstance, Third Party Vendors will pull financial payment data previously entered by PAP into PAP's private customer account on Broker Service 106 for a specific Third Party Vendor. The PAP additionally can make arrangements for payment while in a chat session with a Third Party Vendor, or use various other forms of payment on file in a PAP's private customer account on Broker Service 106.

In various embodiments, System 100 may perform bi-directional interactive audio, visual, audio-visual, data, signaling and content communication, using Broker Service 106 and various premises based devices (PCNs 102) (together referred to as "Communication Content" delivery system). Today many people can look up a person's telephone number, view it on caller ID, and/or find it in business' contact lists, etc. Also a person's telephone privacy or quiet time is disrupted by calls being received that are misdialed at all hours of the day and night, dialed by telemarketers regardless if a person has registered on the Federal Do Not Call List, calls from unknown people that are received with no caller-ID information, legitimate calls received at other undesirable times, etc., simply because all that a caller needs to do is dial direct to practically any seven or ten digit number combination. Further, in many social, professional and business settings people find it necessary to give out their traditional telephone numbers, but do so half-heartedly and with trepidation knowing that the given telephone number(s) will be in the hands of many people forever, thus should the giving party not want to communicate with the other party again, the giving party must depend only upon the good-will of the receiving persons never to call or use the received number again. Additionally, some people desiring to "mask" their telephone identity sometimes use other people's or entity's telephone(s), thus shifting the exposure to risk and/or annoyance to other unassuming people and entities. People are highly communicative and find it desirable to frequently use their telephone, but have additional common concerns: the caller generally believes it's the right time to call, but seldom knows for sure that it is without actually calling and risking bothering the called party with untimely conversation or bothering the called party with only the noise of the telephone ringing, people often call numbers that are found to be obsolete, cancelled or changed, thus again bothering the called party, to name but a few concerns and annoyances of using traditional telephone architecture and common practices.

In various embodiments, Broker Service 106 of System 100 may be used to establish bi-directional interactive audio, visual, audio-visual, data, signaling and content communication, together referred to as "Communication Content" relationships with a variety of entities such as, but not limited to: families, close, casual or new friends and selected individuals, professional services, Third Party Vendors and their various partners and/or suppliers, information and other content providers, emergency announcement services and combinations thereof using selected PCN 102, Programming Device 104 and/or any other object of connectivity supported by the System 100, and for the purposes of this document, will be referenced as Interactive Property Communication System ("IP Communication System").

An initial user of the IP Communication System of Broker Service 106 of System 100 may register their account on Broker System 106 of System 100. For the purpose of this document, such users shall each be called a Person at the Property ("PAP"). After completing initial registration on Broker Service 106, Administrator may, utilizing selected PCN(s) 102, Programming Device(s) 104, and/or any other object of connectivity supported by the System 100, register a particular PAP and each other user (referenced as a "Guest" herein) who will be using a PAP's IP Communication System by listing in some situations (but not limited to or made mandatory in all situations) the name of each Guest. The System will then assign and include in the listing a general and/or unique Guest primary code ("Guest Primary Code"); a secondary Guest code ("Guest Secondary Code"). In various embodiments, a Guest voice recording is personally made by each Guest and stored on Broker Service 106 of System 100 for subsequent Guest voice recognition and validation ("Guest Voice Validation") applications. In various embodiments this allows for recognition and/or validation of a Guest via Broker Service 106 for subsequent transmission of Guest's Communication Content to IP Communication System's selected PCN(s) 102, Programming Device(s) 104, and/or any other object or device of connectivity supported by the System 100. In various embodiments programmable exceptions can be made if the Broker Service 106 cannot properly recognize or validate the Guest's voice. Such cases might include, but are not limited to, illness, poor reception, or other changes that make the Guest's contact more important than a necessary voice recognition and/or validation.

In various embodiments, the listing may include Guest contact information, but not limited to, call back telephone numbers and other IP Communication System Guest Addresses. In various embodiments, the System 100 may record a Guest assignment by a PAP to optional groups and/or classifications such as, but not limited to, family, friend, social or new casual acquaintance, (named) Third Party Vendor, (named) medical clinic, (named) personal doctor, (named) auto insurance company, federal, state or local authorities for weather, catastrophe, emergency alert or other general alert or important information.

In various embodiments, the Guest name and other announcement information that is selected by a PAP may be transmitted by and through Broker Service 106 to the IP Communication System's selected PCN(s) 102 Identification 255 locations, Programming Device(s) 104, and/or any other object of connectivity supported by the System 100. In various embodiments, the system will support individual Guest multiple answering priority levels with paired multiple Guest Addresses allowing processing of various priority delivery levels of Communication Content: by way of example, a (named) Health Clinic calling with life threatening communication requiring immediate PAP contact is assigned by the PAP a high priority level with a unique Guest Addresses, or a (named) Health Clinic calling with general or no urgent communication is assigned by the PAP a lower priority level (and may be programmed with one or more different Guest Addresses).

In various embodiments, a PAP may assign a (named) Third Party Vendor to a high priority by assigning one or more high priority Guest Addresses. Some applications include, but are not limited to, assignment of higher priority addresses to immediately receive a specific and valuable short-lived offer, such as a last minute seat on an airline at a price and/or terms previously requested by the PAP. In various embodiments, the PAP may make a selection of IP Communication System transmission technologies and methods, such as, but not limited to, ranging from single communication technology up to redundant, cascading, availability and/or backup communication technologies and methods along with selection of associated costs; programming of PAP's IP Communication System operations and functions, including but not limited to, hourly, days, calendar, holiday ranges; number of repeated announcements with selected time intervals between announcements for specified Guests calling in and PAP's selection of automatic or manually selected message storage for specific Guests' calls carrying Communication Content.

When an announcement limit is reached for a specific Guest calling, the Guest announcements may be, but are not limited to, automatic routing to memory on selected PAP's PCNs 102, Programming Devices 104, the PAP's personal member account page on the Broker Service 106 and/or any other object of connectivity supported by the System 100 for a PAP's future retrieval and further processing, activation of specified received call(s) message stored alerts such as, but not limited to, audio, visual, text and graphic symbol indicating a message(s) has been automatically stored on the selected PCNs 102, Programming Devices 104, the PAP's personal member account page on the Broker Service 106 and/or any other object of connectivity supported by the System 100 for retrieval and further processing.

Additionally, upon receiving any PAP Guest Communication Content call on a PAP's PCN 102, Programming Device 104, and/or any other object of connectivity supported by the System 100, a PAP may at any time speak or physically enter a command into PAP's selected PCN(s) 102, Programming Device(s) 104, and/or any other object of connectivity supported by the System 100 to immediately force the received call into stored memory on PAP's selected PCN(s) 102, Programming Device(s) 104, a PAP's personal member account page on the Broker Service 106 and/or any other object of connectivity supported by the System 100. In various embodiments, the System 100 may activate specified received Communication Content message call(s) stored by announcing and/or displaying alerts such as, but not limited to, audio, visual, text and graphic symbols indicating a message(s) that may have been automatically stored on the PAP's selected PCN(s) 102, Programming Device(s) 104, a PAP's personal member account page accessible to the Broker Service 106 and/or any other object of connectivity supported by the System 100 for retrieval and further processing.

On a PAP's initial setup of the PAP's IP Communication System personal subscriber account page, a PAP may be assigned by the Broker Service 106, including but not limited to, one or more traditional telephone numbers, IP addresses and any other type, category or technology required addresses ("PAP Addresses") to allow a PAP to distribute to the PAP's Guests groups and/or classifications one or more of, family, friend, social or new casual acquaintance, (named)Third Party Vendor, (named) medical clinic, PAP's (named) personal doctor, family (named) auto insurance company and Federal, State or local authorities for weather, catastrophe, emergency alert or other general alert or important information. In various embodiments, this allows the PAP's Guests to program and/or utilize Broker Service 106 and PAP assigned PAP Addresses to make any type Communication Content calls to a PAP specifically ranging from PAP individually assigned high to low communication priority utilizing specific and appropriate PAP Addresses to PAP's Broker Service 106 account for subsequent re-transmission authorized by Broker Service 106 and PAP to PAP's selected PCN(s) 102 general or specific Identification 255 location(s), Programming Device(s) 104, and/or any other object of connectivity supported by the System 100.

Upon a PAP hearing and/or seeing an incoming communication announcement from a registered PAP Guest on the PAP's selected PCN(s) 102 general or specific Identification 255 location(s), Programming Device(s) 104, and/or any other object of connectivity supported by the System 100, PAP can use, including but not limited to, the following answering options: answer the PAP Guests communication by verbally stating a PAP Command, PAP automatically or manually selecting Guest Voice Validation or physically touching or entering a PAP Guest Code into the PAP's selected PAP's PCN(s) 102, Programming Device(s) 104, and/or any other object of connectivity supported by the System 100, a PAP Command, to perform, including but not limited to, answering, not answering or forwarding the PAP Guests' Communication Content to memory on a selected PAP's PCN(s) 102, Programming Device(s) 104, the PAP's personal member account page on the Broker Service 106 and/or any other object of connectivity supported by the System 100 for PAP's future retrieval and further processing, have the PAP's Guest's Communication Content follow the PAP on the PCN(s) 102 where the PAP travels in the property or elsewhere where the PAP's or PCN(s) 102 belonging to other PAP's control are located, shutting off automatically or manually the PAP 102's that are geographically behind and/or no longer needed, have additional, specific or all PAP 102's activate, PAP Command that the PAP 102's being utilized activate and/or deactivate any associated Sensor 253 such as, but not limited to, microphone, motion detector, camera, or other annunciators or sensors as may be deployed at a location.

The present system provides a highly programmable access mechanism that can be specially programmed for specific users and specific communication control needs. In one example, a PAP has the option to program the System 100 to assign to a specific person in a specific family group the certain required and optional registration information of the PAP Guest. This feature allows a PAP the ability to "delegate" communication and content control to a proxy, such as a trusted friend, relative, or spouse. Other communication proxies can be programmed into the system to tailor the access for any given situation and the examples given herein are for demonstrating the system and are not intended to be exclusive, exhaustive or limiting of the present system 100.

A PAP may geographically transit to other areas served by PCNs 102. The system 100 allows a PAP using a PCN 102, programming device 104, Broker Service 106, cellular phone and/or any other object of connectivity supported by the System 100 or other device adapted to communicate with the Broker Service 106 to log onto the PAP's respective private customer account and enter different PCN identification number(s) of identification 255 to perform communications with the Broker Service 106 from a variety of different geographic locations. The selection of PCNs 102 can be programmed to be, but not limited to, on and/or off at a particular date and time, programmed to be left in an on or off status generally, or programmed to automatically turn off or on upon a specific date and time. Any number of exceptions can be made so that specified PCNs 102 under the control of a PAP can be selected/programmed to be "on" for emergency messaging or emergency bi-directional communications as specifically selected by the PAP having primary control over an inventory of PCN 102 Identification numbers Identification 255. When communication to a selected PCN 102 is desired, the Broker Service 106 can be programmed to allow and direct that in and/or out communication from and to a specific PCN 102 based upon the PAP's communication specifications and directions as specified by the PAP on its PAP private customer account on Broker Service 106. In certain circumstances and as authorized by the PAP, certain limited up to full PAP customer rights can be assigned to other person's or parties to aid primary PAP in executing primary PAP's desires. One example of this may be a primary PAP who is for various reasons not available to receive or make communications and/or purchasing or other decisions, and the primary PAP desires and authorizes a secondary, or more, person or party to assume some up to full control of the primary PAP's control, operation and administration of the primary PAP's customer account on Broker Service 106. The primary PAP may, but not be limited to, assign certain date and time ranges to the newly created and authorized secondary person(s) and/or party(s) that allow the newly created and authorized person(s) or party(s) to automatically have cancelled their rights assigned by the primary PAP, or any combination of authorization programming to another person(s) or party(s).

When a PAP desires to geographically transit to other areas served by PCN(s) 102 that are not under the control of the PAP, the PAP using a PCN 102, Programming Device 104 and/or any other object of connectivity supported by system 100 or other device logs on to the PAP's respective private customer account at Broker Service 106 and makes request to add additional PCN 102 Identification number(s) Identification 255 belonging to and under the control of a different PAP. Examples would be, not limited to, the travel industry. If a primary PAP purchased an airline ticket to travel, either through the primary PAP's PCN 102, Programming Device 104 and/or any other object of connectivity supported by system 100 directly connecting to the broker service 106's registered and PAP's requested and accepted Third Party Vendor airline, through a travel bureau, directly from the airline or purchased through some other source provider of the purchased ticket, the primary PAP traveling could register their future non-controlled or owned PCN 102 connectivity session by requesting through their personal account on the Broker Service 106 that all or some of their inbound messages be repeated and/or re-routed by the Broker Service 106 from the PAP's controlled PCN(s) 102 identification number(s) Identification 255, through the Broker Service 106 to the airlines communication link to the PAP's specific aircraft seat's installed PCN 102 or to the primary PAP's Programming Device 104 and/or any other object of connectivity supported by system 100. Because the Third Party Vendor airline knows of the primary PAP's flight reservation schedule and seat assignment in real-time, the Third Party Vendor airline can allow Broker Service 106 to follow primary PAP's seat assignment throughout their travel while on-board their aircraft.

Additionally, to accommodate any changes in seats, the primary PAP would while at their actual seat sign into the Third Party Vendor's PCN 102 to log on to Broker Service 106 of System 100 for bi-directional service, thus preventing miss-directed calls and PCN 102 usage by a non-authorized PAP or other non-authorized person. Additionally, when a PAP temporarily or permanently leaves their actual seat they may log off temporarily or permanently preventing usage by non-authorized PAPs or other persons. When the primary PAP's flight(s) is concluded, the primary PAP requested message repeating and/or forwarding order requested at Broker Service 106 is terminated by either the subject airline owning and controlling the assigned PCN's 102 identification 255 and/or the primary PAP. Alternatively, but not limiting, the Broker Service 106 can forward the primary PAP's requested inbound messages from the Broker Service 106 directly to the PAP's Programming Device 104.

Additionally, similar to the primary PAP's airline ticket purchase options, but not limited by, available to PAP to purchase an airline ticket specified herein, the PAP makes a reservation with a hotel or lodging facility ("Hotel") that is a Third Party Vendor of Broker Service 106 or an individual subscriber of Broker Service 106 of System 100 with their own PCN 102, Programming Devices 104 and/or any other object of connectivity supported by system 100, and has installed PCN 102's in certain or all rooms and selected or all other areas of the Hotel's property. Upon check-in at the Hotel providing PCN 102 service and use by guests and others, the Hotel approves and activates the guest PAP's forwarding request placed earlier on the Broker Service 106 by a guest PAP to the Hotel's owned and controlled PCN's 102 identification number(s) of identification 255 located in the Hotel's guest room assigned to guest PAP. Additionally, the Hotel can approve additional other Hotel-owned PCN 102 identification numbers 255 where the guest PAP may travel within the Hotel-owned area, thus allowing notification following and requested and allowed information to a guest PAP with the use of Hotel assigned code or pin allowing guest PAP access Hotel's PCN 102(s). When a guest PAP checks-out of subject Hotel, the guest PAP's prior requested message repeating and/or forwarding order to subject the Hotel's owned and controlled PCN 102(s) is either cancelled by subject Hotel and /or guest PAP at any time by either guest PAP or Hotel terminating message following request on guest PAP and/or Hotel's individual personal and private account at the Broker Service 106.

Alternatively, among other things, the Broker Service 106 can then repeat and/or forward the primary PAP's requested inbound messages from the Broker Service 106 directly to the PAP's programming device 104 and/or any other object of connectivity supported by System 100 with no break in notification service or connectivity from the Broker Service 106 to a primary PAP. Thus, it can readily be seen and understood that wherever a PAP travels, a PAP can request through their personal and private account on the Broker Service 106 both repeat and forwarding connectivity to any other non-owned PCN(s) 102, Programming Device(s) 104 and/or any object of connectivity supported by the system 100 and its identification number(s) 255 allowing Third Party Vendor(s) and their partner(s) notification to PAP of requested goods and/or services offerings matching PAP's pricing, terms and conditions, if necessary and at PAP specified time, frequency, duration and other PAP notification and recording settings to any and all non-owned or managed PCN 102's, Programming Devices 104 and/or any object of connectivity supported by the system 100.

The PAP may use owned or managed PCN(s) 102, Programming Device(s) 104 and/or any other objects of connectivity supported by System 100 to connect to Broker Service 106 to manage a PAP's personal and private account to, but not limited by, query, view, add, change, delete and/or request addition of authorized Third Party Vendor's goods and services of Broker Service 106 and edit and/or manage all PAP personal and private account information such as, but not limited to, private codes, financial information, announcement and notification settings, contact information, billing and payment account numbers, codes and authorizations, additional authorized person's or entities access to manage various authority levels of primary PAP account and specific duties and authorization codes, etc.

Similarly, it is understood that in some embodiments, a requesting PAP may use owned and managed PCN(s) 102, Programming Device(s) 104 and/or any other object(s) of connectivity supported by System 100 to request through Broker Service 106 use of and receive, but not limited to, approval, specific pin-codes, dates and times of use, etc. to non-owned and/or non- managed specific PCN 102, Programming Device 104 and/or any other object of connectivity supported by system 100 to connect to Broker Service 106 to manage requesting PAP's personal and private account to, but not limited to, query, view, add, change, delete and/or request addition of authorized Third Party Vendor's goods and services of Broker Service 106 and edit and/or manage all PAP account information such as, but not limited to, private codes, financial information, announcement and notification settings, contact information, billing and payment account numbers, codes and authorizations, additional authorized person's or entities access to manage various authority levels of a primary PAP account and specific duties and authorization codes, etc.

Medical Wellness

The present system brings opportunities for wellness checks and "virtual visits" to the sick or aged. These functions can be supported by the present system and in combination with other medical services in conjunction with the broker service to provide the wellness checking, virtual visits, medication reminders, medication refill subscriptions or any other host of medication related services. For example, the subscriber could allow a health care provider access to certain information via the broker service to perform wellness checks or to review medication history, activity data, among a host of other things.

Day to day health is supported by this interactive, bidirectional system. And the services can be supported by the subscriber's activities, by the medical care provider, by a scheduled approach, and/or by all of them.

The PCN 102 can also be used in case of a trip and fall incident. For example, if a person is near a PCN 102 and shouts out "Help" or "I need help," the PCN 102 can be programmed to contact a variety of services, including, the broker server 106, 911 emergency services, loved ones or others trusted to lend assistance. The communications can take form in any programmed operation and a live communication to such destinations can also take place, as programmed by the system.

The possible uses are unlimited and the examples given herein are intended to demonstrate some of the rich programmability and advantages of the present system.

Security

The present PCN system allows for a new type of security for subscribers. It is a security system that 'follows' the subscriber from location to location on a property fitted with PCNs, and from property to property for multiple locations fitted with PCNs. That affords the subscriber a security system with a monitoring service that travels as the do and as they program it to operate. The system also provides the ability for a number of PCNs to conduct independent direct communications with the broker service to provide redundant lines of communication for safety and assistance. The possible uses are unlimited and the examples given herein are intended to demonstrate some of the rich programmability and advantages of the present system.

Emergency Communication Network

The system can be connected to the FEMA IPAWS network established and mandated by Congress. Emergency information can be spread using PCNs in addition to or in lieu of traditional distribution mechanisms (e.g., siren). Such emergency communications can survive a natural disaster for a certain time due to embodiments featuring battery backup and a plurality of direct communications options as set forth herein. The possible uses are unlimited and the examples given herein are intended to demonstrate some of the rich programmability and advantages of the present system.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

The invention claimed is:

1. A method of communicating with a plurality of property communication devices configured for placement at various premises for providing communications to a plurality of subscribers, the method comprising:
   receiving instructions associated with at least one of the plurality of subscribers, the instructions defining parameters associated with receipt of communications over one or more of the plurality of property communication devices;
   programming a server-based system to control the communications with the at least one subscriber based on the instructions;
   receiving, from a plurality of third parties, the communications configured to be communicated over a wireless network;

without intervention from one of the subscribers, receiving information from one or more of the plurality of property communication devices that indicates a location with respect to at least one relevant property communication device where the at least one subscriber may receive one of the communications to focus delivery of the one of the communications to the at least one relevant property communication device and to the at least one subscriber; and providing the one of the communications to the at least one subscriber from the server-based system to the at least one relevant property communication device, such that the one of the communications provided meets the parameters programmed for the at least one subscriber.

2. The method of claim 1, wherein at least one of the plurality of third parties comprises a third party vendor, wherein the communications provided comprise advertising content from the third party vendor, the method further comprising:
notifying the at least one subscriber of the advertising content using an annunciator configured into the plurality of property communication devices.

3. The method of claim 1, wherein receiving instructions associated with at least one subscriber comprises registering the plurality of third parties, the method further comprising:
storing a voice recording of at least one of the registered third party, wherein the communications from the at least one registered third party is provided to the plurality of subscribers based on the voice recording.

4. The method of claim 1, wherein receiving instructions associated with at least one subscriber comprises registering the plurality of third parties, the method further comprising:
assigning a code associated with at least one of the registered third party, wherein the communications from the at least one registered third party is provided to the plurality of subscribers based on the assigned code.

5. The method of claim 1, wherein receiving instructions associated with at least one subscriber comprises registering the plurality of third parties, wherein the defined parameters comprise a classification of the at least one registered third party, the method further comprising:
assigning at least one priority level to the communication to the one or more of the property communication devices based on the classification of the third party.

6. The method of claim 5, wherein the at least one registered third party is a third party vendor, the method comprising:
assigning a high priority level to the third party vendor.

7. The method of claim 5, wherein the at least one registered third party is a health clinic, the method comprising:
assigning a high priority level to the health clinic.

8. The method of claim 5, wherein assigning at least one priority level to the communication to the one or more of the property communication devices based on the classification of the third party comprises assigning a first communication network to a first priority level and a second communication network to a second priority level.

9. The method of claim 8, wherein assigning a first communication network to a first priority level and a second communication network to a second priority level comprises assigning a first cellular network to the first priority level and assigning a second cellular network to the second priority level.

10. The method of claim 5, wherein the at least one registered third party is a family member.

11. The method of claim 5, wherein the at least one registered third party is a friend.

12. The method of claim 1, wherein the defined parameters comprise a communication limit value associated with one of the third parties, the method further comprising:
forwarding the communication from the third party to a memory device when a number of communications associated with the third party exceeds the communication limit value, wherein the memory device is configured to store one or more communications.

13. The method of claim 1, further comprising:
storing, in a delegate database, information about one or more users authorized to receive communications directed to one of the plurality of subscribers; and
providing the communications to the one or more users authorized to receive communications that were originally directed to one of the plurality of subscribers from the server-based system to one or more of the plurality of property communication devices.

14. The method of claim 13, wherein the one or more users authorized to receive communications is a relative of the one of the plurality of subscribers.

15. The method of claim 1, further comprising:
assigning each of the plurality of third parties to one or more of a plurality of groups;
assigning at least one priority level to each of the plurality of groups; and
assigning at least one priority level to the communication to the one or more of the property communication devices based on the assigned priority level of the group.

16. The method of claim 1, further comprising:
storing a schedule that controls the communications of at least one of the plurality of third parties.

17. The method of claim 16, wherein the stored schedule comprises one or more days of a week.

18. The method of claim 16, wherein the stored schedule comprises one or more hours of a day.

19. The method of claim 16, wherein the stored schedule comprises a number of communications permitted from one of the plurality of third parties.

20. The method of claim 16, wherein the stored schedule comprises a time interval between communications from one of the plurality of third parties.

21. The method of claim 1, further comprising:
receiving, via the at least one subscriber, a command to stop providing the communication; and
storing the communication in a memory device.

22. The method of claim 1, further comprising:
storing, based on at least one defined parameter, a message related to the communication; and
providing an indication to the at least one subscriber that a message has been stored.

23. The method of claim 1, wherein providing the one of the communications to the at least one subscriber from the server-based system to the at least one relevant property communication device, such that the one of the communications provided meets the parameters programmed for the at least one subscriber comprises:
providing the one of the communications to the at least one subscriber by an audio format.

24. The method of claim 1, wherein providing the one of the communications to the at least one subscriber from the server-based system to the at least one relevant property communication device, such that the one of the communications provided meets the parameters programmed for the at least one subscriber comprises:
providing the one of the communications to the at least one subscriber by a video format.

25. The method of claim 1, wherein providing the one of the communications to the at least one subscriber from the server-based system to the at least one relevant property communication device, such that the one of the communications provided meets the parameters programmed for the at least one subscriber comprises:

provide the one of the communications to the at least one subscriber by a text message.

26. The method of claim 1, wherein providing the one of the communications to the at least one subscriber from the server-based system to the at least one relevant property communication device, such that the one of the communications provided meets the parameters programmed for the at least one subscriber comprises:

providing the one of the communications to the at least one subscriber by an email message.

* * * * *